United States Patent
Wei

(10) Patent No.: US 9,307,769 B2
(45) Date of Patent: Apr. 12, 2016

(54) METHOD FOR INCREASING PLANT YIELD, AND YIELD IMPROVING COMPOSITIONS

(71) Applicant: Plant Health Care, Inc., Raleigh, NC (US)

(72) Inventor: Zhongmin Wei, Kirkland, WA (US)

(73) Assignee: Plant Health Care, Inc., Raleigh, NC (US)

( * ) Notice: Subject to any disclaimer, the term of this patent is extended or adjusted under 35 U.S.C. 154(b) by 0 days.

(21) Appl. No.: 14/877,668

(22) Filed: Oct. 7, 2015

(65) Prior Publication Data

US 2016/0021887 A1     Jan. 28, 2016

Related U.S. Application Data

(62) Division of application No. 13/730,301, filed on Dec. 28, 2012, now Pat. No. 9,204,638.

(60) Provisional application No. 61/581,819, filed on Dec. 30, 2011.

(51) Int. Cl.
*A01N 47/44*     (2006.01)
*A01N 47/34*     (2006.01)

(52) U.S. Cl.
CPC ............... *A01N 47/44* (2013.01); *A01N 47/34* (2013.01)

(58) Field of Classification Search
CPC ........................ A01N 47/44; A01N 47/34
See application file for complete search history.

(56) References Cited

U.S. PATENT DOCUMENTS

| | | | |
|---|---|---|---|
| 5,849,868 A | 12/1998 | Beer et al. | |
| 6,277,814 B1 | 8/2001 | Qiu et al. | |
| 7,622,641 B2 | 11/2009 | McCutchen et al. | |
| 7,973,218 B2 | 7/2011 | McCutchen | |
| 2002/0062500 A1 | 5/2002 | Fan et al. | |
| 2004/0016029 A1 | 1/2004 | Wei et al. | |
| 2004/0097596 A1 | 5/2004 | Stuiver et al. | |
| 2007/0037705 A1 | 2/2007 | Wei | |
| 2010/0043095 A1 | 2/2010 | Wei | |

FOREIGN PATENT DOCUMENTS

CN     1231827 A     10/1999
WO     2004/057957 A2     7/2004

OTHER PUBLICATIONS

Wei et al., "Harpin, Elicitor of the Hypersensitive Response Produced by the Plant Pathogen Erwinia amylovora," Science 257:85-88 (1992).
International Search Report for International Patent Application No. PCT/US2012/072269 (Apr. 30, 2013).

*Primary Examiner* — Ali Soroush
(74) *Attorney, Agent, or Firm* — LeClairRyan, a Professional Corporation

(57) ABSTRACT

The present invention relates to a method of increasing yield of a plant. This method involves applying to a plant and/or area of cultivation thiophanate methyl and an isolated hypersensitive response elicitor protein or polypeptide fragment, wherein said applying is carried out under conditions effective to induce a synergistic yield from the plant. The present invention also relates to a composition comprising a liquid or solid carrier, thiophanate methyl, and an isolated hypersensitive response elicitor protein or polypeptide fragment.

17 Claims, 2 Drawing Sheets

Calculation of % Increase in Yield for Dry Beans

| Trial | Mean Yield for Each trial - (Bu/Acre) | | | | % Increase in Individual Trials | | |
|---|---|---|---|---|---|---|---|
| | UTC | PHC-351 | Topsin® | Combination | PHC-351 | Topsin® | Combination |
| A | 52.67 | 53.31 | 54.51 | 53.04 | 1.20% | 3.50% | 0.70% |
| B | 22.96 | 22.91 | 22.51 | 27.81 | -0.30% | -2.00% | 21.10% |
| C | 12.57 | 13.37 | 15.43 | 18.27 | 6.40% | 22.8% | 45.4% |
| D | 21.20 | 21.60 | 23.00 | 23.50 | 1.90% | 8.50% | 10.8% |
| E | 25.78 | 28.12 | 35.66 | 37.41 | 9.10% | 38.3% | 45.1% |
| F | 13.02 | 14.22 | 24.16 | 27.21 | 9.20% | 85.6% | 109% |
| G | 57.10 | 56.60 | 57.00 | 58.50 | -0.90% | -0.20% | 2.50% |
| H | 27.90 | 28.59 | 29.36 | 32.04 | 2.50% | 5.20% | 14.9% |
| I | 23.20 | 27.24 | 38.10 | 40.16 | 17.4% | 64.3% | 73.1% |
| J | 44.15 | 48.75 | 52.54 | 48.65 | 10.4% | 19.0% | 10.2% |
| K | 38.48 | 37.04 | 40.32 | 40.94 | -3.74% | 4.77% | 6.39% |
| L | 21.56 | 17.70 | 23.80 | 24.70 | -17.9% | 10.4% | 14.6% |
| M | 39.25 | 42.93 | 48.72 | 47.93 | 9.36% | 24.1% | 22.1% |
| N | 51.45 | 54.64 | 53.43 | 55.65 | 6.21% | 3.86% | 8.16% |
| O | 31.98 | 32.90 | 32.85 | 34.37 | 2.88% | 2.73% | 7.48% |
| P | 33.16 | 34.40 | 35.33 | 36.39 | 3.75% | 6.56% | 9.76% |
| Grand Mean | 32.28 | 33.39 | 36.67 | 37.91 | 3.59% | 18.6% | 25.1% |

*FIG. 1*

Calculation of % Increase in Yield for Peanuts

| Trial # | Mean Yield for Each trial - (Lb/Acre) | | | | % Increase in Individual Trials | | |
|---|---|---|---|---|---|---|---|
| | UTC | PHC-351 | Topsin® | Combination | PHC-351 | Topsin® | Combination |
| AA | 5769 | 5606 | 5774 | 5682 | -2.8% | 0.1% | -1.5% |
| BB | 5960 | 5502 | 6309 | 6483 | -7.7% | 5.8% | 8.8% |
| Grand Mean | 5865 | 5554 | 6042 | 6083 | -5.3% | 3.0% | 3.6% |

*FIG. 2*

SEQUENCE LISTING

```
<160> NUMBER OF SEQ ID NOS: 2

<210> SEQ ID NO 1
<211> LENGTH: 412
<212> TYPE: PRT
<213> ORGANISM: artificial
<220> FEATURE:
<223> OTHER INFORMATION: Harpin fusion protein

<400> SEQUENCE: 1

Met Ser Leu Asn Thr Ser Gly Leu Gly Ala Ser Thr Met Gln Ile Ser
1               5                   10                  15

Ile Gly Gly Ala Gly Gly Asn Asn Gly Leu Leu Gly Thr His Met Pro
            20                  25                  30

Gly Thr Ser Ser Ser Pro Gly Leu Phe Gln Ser Gly Gly Asp Asn Gly
        35                  40                  45

Leu Gly Gly His Asn Ala Asn Ser Ala Leu Gly Gln Gln Pro Ile Asp
    50                  55                  60

Arg Gln Thr Ile Glu Gln Met Ala Gln Leu Leu Ala Glu Leu Leu Lys
65                  70                  75                  80

Ser Leu Leu Asp Ser Gly Glu Lys Leu Gly Asp Asn Phe Gly Ala Ser
                85                  90                  95

Ala Asp Ser Ala Ser Gly Thr Gly Gln Gln Asp Leu Met Thr Gln Val
            100                 105                 110

Leu Asn Gly Leu Ala Lys Ser Met Leu Asp Asp Leu Leu Thr Lys Gln
        115                 120                 125

Asp Gly Gly Thr Ser Phe Ser Glu Asp Asp Ser Gly Pro Ala Lys Asp
    130                 135                 140

Gly Asn Ala Asn Ala Gly Ala Asn Asp Pro Ser Lys Asn Asp Pro Ser
145                 150                 155                 160

Lys Ser Gln Gly Pro Gln Ser Ala Asn Lys Thr Gly Asn Val Asp Asp
                165                 170                 175

Ala Asn Asn Gln Asp Pro Met Gln Ala Leu Met Gln Leu Leu Glu Asp
            180                 185                 190
```

```
Leu Val Lys Leu Leu Lys Ala Ala Leu His Met Gln Gln Pro Gly Gly
        195                 200                 205

Asn Asp Lys Gly Asn Gly Val Gly Gly Asp Ser Gly Gln Asn Asp Asp
    210                 215                 220

Ser Thr Ser Gly Thr Asp Ser Thr Ser Asp Ser Ser Asp Pro Met Gln
225                 230                 235                 240

Gln Leu Leu Lys Met Phe Ser Glu Ile Met Gln Ser Leu Phe Gly Asp
                245                 250                 255

Glu Gln Asp Gly Thr Asp Ser Thr Ser Gly Ser Arg Phe Thr Arg Thr
            260                 265                 270

Gly Ile Gly Met Lys Ala Gly Ile Gln Ala Leu Asn Asp Ile Gly Thr
        275                 280                 285

His Ser Asp Ser Ser Thr Arg Ser Phe Val Asn Lys Gly Asp Arg Ala
    290                 295                 300

Met Ala Lys Glu Ile Gly Gln Phe Met Asp Gln Tyr Pro Glu Val Phe
305                 310                 315                 320

Gly Lys Pro Gln Tyr Gln Lys Gly Pro Gly Gln Glu Val Lys Thr Asp
                325                 330                 335

Asp Lys Ser Trp Ala Lys Ala Leu Ser Lys Pro Asp Asp Asp Gly Met
            340                 345                 350

Thr Pro Ala Ser Met Glu Gln Phe Asn Lys Ala Lys Gly Met Ile Lys
        355                 360                 365

Ser Ala Met Ala Gly Asp Thr Gly Asn Gly Asn Leu Gln Ala Arg Gly
    370                 375                 380

Ala Gly Gly Ser Ser Leu Gly Ile Asp Ala Met Met Ala Gly Asp Ala
385                 390                 395                 400

Ile Asn Asn Met Ala Leu Gly Lys Leu Gly Ala Ala
                405                 410

<210> SEQ ID NO 2
<211> LENGTH: 1239
<212> TYPE: DNA
<213> ORGANISM: artificial
<220> FEATURE:
<223> OTHER INFORMATION: Coding sequence for Harpin fusion protein

<400> SEQUENCE: 2
atgagtctga atacaagtgg gctgggagcg tcaacgatgc aaatttctat cggcggtgcg    60
ggcggaaata cgggttgctg ggtacgcat atgcccggga cctcgtcctc gccgggtctg    120
ttccagtccg gggggacaa cgggcttggt ggtcataatg caaattctgc gttgggcaa     180 caacccatcg atcggcaaac cattgagcaa atggctcaat tattggcgga actgttaaag    240
tcactgctag atagtgggga aaagctcggt gacaacttcg gcgcgtctgc ggacagcgcc    300
tcgggtaccg acagcagga cctgatgact caggtgctca atggcctggc caagtcgatg    360
ctcgatgatc ttctgaccaa gcaggatggc gggaccagct ctccgaaga cgatagtggg    420 ccggcgaagg acggcaatgc caacgcgggc gccaacgacc cgagcaagaa cgacccgagc    480
aagagccagg gtccgcagtc ggccaacaag accggcaacg tcgacgacgc caacaaccag    540
gatccgatgc aagcgctgat gcagctgctg aagacctgg tgaagctgct gaaggcggcc    600
ctgcacatgc agcagcccgg cggcaatgac aagggcaacg gcgtgggcgg tgatagtggg    660
caaaacgacg attccacctc cggcacagat tccacctcag actccagcga cccgatgcag    720
cagctgctga agatgttcag cgagataatg caaagcctgt ttggtgatga gcaagatggc    780
```

-continued

```
accgatagta ctagcggctc gaggtttact cgtaccggta tcggtatgaa agcgggcatt      840
caggcgctga atgatatcgg tacgcacagc gacagttcaa cccgttcttt cgtcaataaa      900
ggcgatcggg cgatggcgaa ggaaatcggt cagttcatgg accagtatcc tgaggtgttt      960
ggcaagccgc agtaccagaa aggcccgggt caggaggtga aaaccgatga caaatcatgg     1020
gcaaaagcac tgagcaagcc agatgacgac ggaatgacac cagccagtat ggagcagttc     1080
aacaaagcca agggcatgat caaaagcgcc atggcgggtg ataccggcaa cggcaacctg     1140
caggcacgcg gtgccggtgg ttcttcgctg ggtattgatg ccatgatggc cggtgatgcc     1200
attaacaata tggcacttgg caagctgggc gcggcttaa                            1239
```

METHOD FOR INCREASING PLANT YIELD, AND YIELD IMPROVING COMPOSITIONS

This application is a division of U.S. patent application Ser. No. 13/730,301, filed Dec. 28, 2012, which claims priority of U.S. Provisional Patent Application Ser. No. 61/581,819, filed Dec. 30, 2011, which is hereby incorporated by reference in its entirety.

FIELD OF THE INVENTION

This invention relates to a method for increasing yield of a plant, and compositions for improving yield of a plant.

BACKGROUND OF THE INVENTION

In crop production, there is a continuous need for agricultural compositions and treatments that improve the health of plants. Healthier plants are desirable since they result in better yields and/or a better quality of the plants or crops. Healthier plants also better resist biotic and/or abiotic stress. A high resistance against biotic stresses in turn allows a lower quantity of applied pesticides, which can then slow down the development of resistances against the respective pesticides.

Hypersensitive response ("HR") elicitor proteins (also known as harpin proteins) elicit disease resistance in plants and increase plant growth. U.S. Pat. No. 6,277,814 describes a method of enhancing growth in plants, which involves applying an HR elicitor polypeptide or protein in a non-infectious form to plants or plant seeds under conditions to impart enhanced growth to the plants or to plants grown from the plant seeds. These methods are carried out to affect any form of plant growth enhancement or promotion, including greater yield, increased quantity of seeds produced, increased percentage of seeds germinated, increased plant size, greater biomass, more and bigger fruit, earlier fruit coloration, and earlier fruit and plant maturation. Early germination and early maturation permit crops to be grown in areas where short growing seasons would otherwise preclude their growth in that locale. Increased percentage of seed germination results in improved crop stands and more efficient seed use. Greater yield, increased size, and enhanced biomass production allow greater revenue generation from a given plot of land.

Agricultural compositions containing isolated HR elicitor proteins have been used to improve plant health and increase yield. For example, PCT Publication No. WO 04/057957 to Wei teaches increasing the efficacy of an agricultural chemical by applying at least one agricultural chemical and at least one HR elicitor protein or polypeptide to a plant or plant seed under conditions effective to increase the efficacy of the agricultural chemical.

There is a need for agricultural compositions and plant treatments that offer a synergistic effect on plant yield, meaning the combined effects of the agents is greater than the additive effects of each individual agent.

The present invention is directed to overcoming these limitations in the art.

SUMMARY OF THE INVENTION

One aspect of the present invention relates to a method of increasing yield of a plant. This method involves applying to a plant and/or area of cultivation thiophanate methyl and an isolated hypersensitive response elicitor protein or polypeptide fragment, wherein said applying is carried out under conditions effective to induce a synergistic yield increase from the plant.

Another aspect of the present invention relates to a composition comprising a liquid or solid carrier, thiophanate methyl, and an isolated hypersensitive response elicitor protein or polypeptide fragment.

The present invention relates to increasing the yield of a plant by application of agents that when applied together or in sequence have a synergistic effect on plant yield. The agents include at least the fungicide thiophanate methyl (or another benzimidazole fungicide) and an isolated hypersensitive response elicitor protein or polypeptide fragment.

As demonstrated in the accompanying Examples, the combined effects of thiophanate methyl and an isolated hypersensitive response elicitor polypeptide designated PHC-351 (Plant Health Care, Inc., Pittsburgh, Pa.) demonstrate in pinto beans and peanut a surprisingly synergistic effect of the two agents on plant yields.

BRIEF DESCRIPTION OF THE DRAWINGS

FIG. 1 is a table showing the results from an experiment testing the control of white mold in pinto bean plants by applying to the plants PHC-351 and thiophanate methyl treatments individually and in combination. The results show the calculation of percent increase in yield in pinto bean plants.

FIG. 2 is a table showing the results of an experiment testing the control of white mold in peanut plants by applying to the plants PHC-351 and thiophanate methyl treatments individually and in combination. The results show the calculation of percent increase in yield.

DETAILED DESCRIPTION OF THE INVENTION

The present invention relates to a method of increasing yield in a plant, and compositions useful in increasing plant yield.

According to the method of the present invention, the fungicide thiophanate methyl and an isolated hypersensitive response elicitor protein or polypeptide fragment are applied to a plant and/or area of cultivation under conditions effective to induce a synergistic yield from the plant in response to said applying.

The phrase "area of cultivation" means any type of environment, soil, area, or material where the plant is growing or intended to grow.

As used herein, the term "plant" includes all parts of a plant, including herbaceous vegetation, leaves, roots, stems, floral structures, pollen, etc. In addition, "plant" means all plants and, particularly, plants of economic importance. Plants may be categorized into agricultural, silvicultural, ornamental, and horticultural plants, based on their human use and/or consumption. In addition, "plants" include natural or wildtype plants, and plants that have been genetically modified.

"Agricultural" plants are plants of which a part or all is harvested or cultivated on a commercial scale or which serve as an important source of feed, food, fibers (e.g., cotton and linen), combustibles (e.g., wood, bioethanol, biodiesel, and biomass) or other chemical compounds. Agricultural plants also include vegetables. Thus, agricultural plants include cereals (e.g., wheat, rye, barley, triticale, oats, sorghum, and rice); beet (e.g., sugar beet or fodder beet); leguminous plants (e.g., beans, lentils, peas, alfalfa, and soybean); oil plants (e.g., rape, oil-seed rape, canola, *juncea* (*Brassica juncea*), linseed, mustard, olive, sunflower, cocoa bean, castor oil plants, oil palms, ground nuts, and soybean); cucurbits (e.g., squash, cucumber, and melon); fiber plants (e.g., cotton, flax, hemp, and jute); vegetables (e.g., cucumbers, spinach, lettuce, asparagus, cabbages, carrots, radish, turnip, celery, chicory, endive, brussel sprouts, parsnip, cauliflower, broccoli, garlic, eggplant, pepper, pumpkin, onions, tomatoes, potatoes, sweet potatoes, cucurbits, and paprika); lauraceous plants (e.g., avocados, cinnamon, and camphor); energy and raw material plants (e.g., corn, soybean, rape, canola, sugar cane, and oil palm); tobacco; nuts (including peanuts); coffee; tea; vines (e.g., table grapes and juice grape vines); hop; stone fruit; apple; blueberry; strawberry; pear; citrus; raspberry; pineapple; sugarcane; turf, natural rubber plants, and marijuana.

"Horticultural plants" are plants commonly used in horticulture and include, without limitation, ornamentals, vegetables, and fruits. "Ornamental" plants are plants which are commonly used in gardening, e.g., in parks, gardens, and on balconies and patios. Non-limiting examples of ornamentals include turf, geranium, pelargonia, petunia, begonia, and fuchsia. Non-limiting examples of vegetables are as described above. Non-limiting examples of fruits include apples, pears, cherries, strawberry, citrus, peaches, apricots, and blueberries.

"Silvicultural" plants are understood to be trees, more specifically, trees used in reforestation or industrial plantations. Industrial plantations generally serve the purpose of commercial production of forest products such as wood, pulp, paper, rubber tree, Christmas trees, or young trees for gardening purposes. Non-limiting examples of silvicultural plants are conifers (e.g., pines), in particular *Pinus* species fir and spruce; *eucalyptus*; tropical trees (e.g., teak, rubber tree, oil palm); willow (*Salix*), in particular *Salix* species; poplar (cottonwood), in particular *Populus* species; beech, in particular *Fagus* species; birch; oil palm; cherry, walnut, and oak.

In one embodiment, the plant used in the method of the present invention is selected from dry bean, peanut, pea, and soybean.

As noted above, the term "plant" also includes plants modified from their wildtype form. Such modifications may occur through breeding, mutagenesis, or genetic engineering (including transgenic and non-transgenic plants). Plants modified by genetic engineering include plants having genetic material that has been modified by the use of recombinant DNA techniques. Such modifications typically include modifications that cannot readily be obtained by cross breeding under natural circumstances, mutations, or natural recombination. Typically, one or more genes have been integrated into the genetic material of a genetically modified plant in order to improve certain properties of the plant. Examples of genetically modified plants are described below.

Plants used in the method of the present invention, e.g., crops which tolerate the action of herbicides, fungicides, or insecticides owing to breeding, including genetic engineering methods, or plants which have modified characteristics in comparison with existing plants, which can be generated by, e.g., traditional breeding methods and/or the generation of mutants, or by recombinant procedures.

In one embodiment, plants to which thiophanate methyl and an isolated hypersensitive response elicitor protein or polypeptide fragment are applied pursuant to the method of the present invention include plants rendered tolerant to the application of specific classes of herbicides. Tolerance to herbicides can be obtained by creating insensitivity at the site of action of the herbicide by expression of a target enzyme which is resistant to herbicide, rapid metabolism (conjugation or degradation) of the herbicide by expression of enzymes which inactivate herbicide, or poor uptake and translocation of the herbicide.

Non-limiting examples include the expression of enzymes which are tolerant to the herbicide in comparison to wild-type enzymes, such as the expression of 5-enolpyruvylshikimate-3-phosphate synthase (EPSPS), which is tolerant to glyphosate (see e.g., "Development and Characterization of a CP4 EPSPS-Based, Glyphosate-Tolerant Corn Event," Heck et al., *Crop Sci.* 45:329-339 (2005); Funke et al., "Molecular Basis for the Herbicide Resistance of Roundup Ready Crops," *PNAS* 103:13010-13015 (2006); U.S. Pat. No. 5,188,642 to Shah et al.; U.S. Pat. No. 4,940,835 to Shah et al.; U.S. Pat. No. 5,633,435 to Barry et al.; U.S. Pat. No. 5,804,425 to Barry et al.; and U.S. Pat. No. 5,627,061 to Barry et al., each of which is hereby incorporated by reference in its entirety); the expression of glutamine synthase, which is tolerant to glufosinate and bialaphos (see e.g., U.S. Pat. Nos. 5,646,024 and 5,561,236 to Leemans et al., which is hereby incorporated by reference in its entirety); and DNA constructs coding for dicamba-degrading enzymes (see e.g., for general reference, U.S. Patent Application Publication No. 2009/0105077 to Bhatti et al. and U.S. Pat. No. 7,105,724 to Weeks et al., each of which is hereby incorporated by reference in its entirety), for dicamba resistance in bean and corn (see PCT Publication No. WO 08/051633 to Monsanto Technology LLC, which is hereby incorporated by reference in its entirety), cotton (see U.S. Pat. No. 5,670,454 to Grossmann et al., which is hereby incorporated by reference in its entirety), pea, potato, sorghum, soybean (see U.S. Pat. No. 5,670,454 to Grossmann et al., which is hereby incorporated by reference in its entirety), sunflower, tobacco, tomato (see U.S. Pat. No. 5,670,454 to Grossmann et al., which is hereby incorporated by reference in its entirety). Gene constructs can be obtained, for example, from microorganisms or plants, which are tolerant to herbicides, such as the *Agrobacterium* strain CP4 EPSPS, which is resistant to glyphosate; *Streptomyces* bacteria which are resistance to glufosinate; *Arabidopsis, Daucus carota, Pseudomonas* ssp., or *Zea mays* with chimeric gene sequences coding for HDDP (see e.g., PCT Publication No. WO 96/38567 to Rhone-Poulenc Agrochimie and PCT Publication No. WO 04/55191 to Biogemma, each of which is hereby incorporated by reference in its entirety); *Arabidopsis thaliana*, which is resistant to protox inhibitors (see e.g., U.S. Patent Application Publication No. 2002/0073443 to Heifetz et al., which is hereby incorporated by reference in its entirety).

Non-limiting examples of commercially available plants with tolerance to herbicides include the corn (maize) varieties Roundup Ready® Corn, Roundup Ready 2® (Monsanto), Agrisure GT®, Agrisure GT/CB/LL®, Agrisure GT/RW® Agrisure 3000GT® (Syngenta), YieldGard VT Rootworm/RR2® and YieldGard VT Triple® (Monsanto) with tolerance to glyphosate; the corn varieties Liberty Link® (Bayer), Herculex I®, Herculex RW®, Herculex® Xtra (Dow, Pioneer), Agrisure GT/CB/LL® and Agrisure CB/LL/RW® (Syngenta) with tolerance to glufosinate; the soybean varieties Roundup Ready® Soybean (Monsanto) and Optimum GAT® (DuPont, Pioneer) with tolerance to glyphosate; the cotton varieties Roundup Ready® Cotton and Roundup Ready Flex® (Monsanto) with tolerance to glyphosate; the cotton variety FiberMax Liberty Link® (Bayer) with tolerance to glufosinate; the cotton variety BXN® (Calgene) with tolerance to bromoxynil; the canola varieties Navigator® and Compass® (Rhone-Poulenc) with bromoxynil tolerance; the canola variety Roundup Ready® Canola (Monsanto) with glyphosate tolerance; the canola variety InVigor (Bayer) with glufosinate tolerance; the rice variety Liberty Link® Rice (Bayer) with glufosinate tolerance and the alfalfa variety Roundup Ready Alfalfa with glyphosate tolerance.

Other plants modified with herbicide are commonly known, and include alfalfa, apple, *eucalyptus*, flax, grape, lentils, oil seed rape, peas, potato, rice, sugar beet, sunflower, tobacco, tomato turf grass, and wheat with tolerance to glyphosate (see e.g., U.S. Pat. Nos. 5,188,642 and 4,940,835 to Shah et al. and U.S. Pat. Nos. 5,633,435, 5,804,425, and 5,627,061 to Barry et al., each of which is hereby incorporated by reference in its entirety); beans, soybean, cotton, peas, potato, sunflower, tomato, tobacco, corn, sorghum and sugarcane with tolerance to dicamba (see e.g., U.S. Patent Application Publication No. 2009/0105077 to Bhatti et al.; U.S. Pat. No. 7,105,724 to Weeks et al.; and U.S. Pat. No. 5,670,454 to Grossmann et al., each of which is hereby incorporated by reference in its entirety); pepper, apple, tomato, millet, sunflower, tobacco, potato, corn, cucumber, wheat, soybean and sorghum with tolerance to 2,4-D (see e.g., U.S. Pat. Nos. 6,153,401 and 6,100,446 to Streber et al.; PCT Publication No. WO 05/107437 to Dow Agrosciences LLC; U.S. Pat. No. 5,608,147 to Kaphammer; and U.S. Pat. No. 5,670,454 to Grossmann et al., each of which is hereby incorporated by reference in its entirety); sugarbeet, potato, tomato, and tobacco with tolerance to glufosinate (see e.g. U.S. Pat. Nos. 5,646,024 and 5,561,236 to Leemans et al., each of which is hereby incorporated by reference in its entirety); canola, barley, cotton, *juncea*, lettuce, lentils, melon, millet, oats, oilseed rape, potato, rice, rye, sorghum, soybean, sugarbeet, sunflower, tobacco, tomato, and wheat with tolerance to acetolactate synthase (ALS) inhibiting herbicides, such as triazolopyrimidine sulfonamides, growth inhibitors and imidazolinones (see e.g., U.S. Pat. No. 5,013,659 to Bedbrook et al.; PCT Publication No. WO 06/060634 to BASF Agrochemical Products, B.V.; U.S. Pat. Nos. 4,761,373, 5,304,732, 6,211,438, 6,211,439, and 6,222,100 to Anderson et al., each of which is hereby incorporated by reference in its entirety); cereal, sugar cane, rice, corn, tobacco, soybean, cotton, rapeseed, sugar beet, and potato with tolerance to HPPD inhibitor herbicides (see e.g. PCT Publication No. WO 04/055191 to Biogemma, PCT Publication No. WO 96/38567 to Rhone-Poulenc Agrochimie, PCT Publication No. WO 97/049816 to E.I. Du Pont De Nemours and Co., and U.S. Pat. No. 6,791,014 to Garcon et al., each of which is hereby incorporated by reference in its entirety); wheat, soybean, cotton, sugar beet, rape, rice, corn, sorghum and sugar cane with tolerance to protoporphyrinogen oxidase (PPO) inhibitor herbicides (see e.g., U.S. Patent Application Publication No. 2002/0073443 to Heifetz et al., U.S. Patent Application Publication No. 2008/0052798 to Dam et al., and Li and Nicholl, "Development of PPO Inhibitor-resistant Cultures and Crops," *Pest Management Science* 61:277-285 (2005), each of which is hereby incorporated by reference in its entirety). The methods of producing such herbicide resistant plants are generally known to persons of ordinary skill in the art, and are described in the references cited herein. Further examples of commercially available modified plants with tolerance to herbicides include CLEARFIELD® Corn, CLEARFIELD® Canola, CLEARFIELD® Rice, CLEARFIELD® Lentils, and CLEARFIELD® Sunflowers (BASF) with tolerance to the imidazolinone herbicides.

Other plants may include those able to synthesize one or more insecticidal proteins, especially those known from the bacterial genus *Bacillus*, particularly from *Bacillus thuringiensis*, such as δ-endotoxins, e.g., CryIA(b), CryIA(c), CryIF, CryIF(a2), CryIIA(b), CryIIIA, CryIIIB(b1), and Cry9c; vegetative insecticidal proteins ("VIP"), e.g., VIP1, VIP2, VIP3, and VIP3A; insecticidal proteins of bacteria colonizing nematodes, e.g., *Photorhabdus* spp. or *Xenorhabdus* spp.; toxins produced by animals, such as scorpion toxins, arachnid toxins, wasp toxins, and other insect-specific neurotoxins; toxins produced by fungi, such Streptomycetes toxins; plant lectins, such as pea or barley lectins; agglutinins; proteinase inhibitors, such as trypsin inhibitors, serine protease inhibitors, patatin, cystatin or papain inhibitors; ribosome-inactivating proteins ("RIP"), such as ricin, corn-RIP, abrin, luffin, saporin, and bryodin; steroid metabolism enzymes, such as 3-hydroxysteroid oxidase, ecdysteroid-IDP-glycosyl-transferase, cholesterol oxidases, ecdysone inhibitors, and HMG-CoA-reductase; ion channel blockers, such as blockers of sodium or calcium channels; juvenile hormone esterase; diuretic hormone receptors (helicokinin receptors); stilben synthase; bibenzyl synthase; chitinases; and glucanases.

The above insecticidal proteins or toxins are to be understood also as pre-toxins, hybrid proteins, truncated, or otherwise modified proteins. Hybrid proteins are characterized by a new combination of protein domains, (see e.g., PCT Publication No. WO 02/015701 to Syngenta Participations AG, which is hereby incorporated by reference in its entirety). Further examples of such toxins or genetically modified plants capable of synthesizing such toxins are disclosed, e.g., in European Patent No. 0374753 and PCT Publication Nos. WO 93/007278 and WO 95/34656, all to Ciba-Geigy AG; European Patent No. 0427529 to Pioneer Hi Bred Int.; European Patent No. 0451878 to Bayer Bioscience NV; and PCT Publication Nos. WO 03/18810 and WO 03/52073 to Syngenta Participations AG, each of which is hereby incorporated by reference in its entirety. Methods for producing such genetically modified plants are generally known to the person of ordinary skill in the art and are described, e.g., in the above-cited references.

These insecticidal proteins contained in the genetically modified plants impart to the plants producing these proteins tolerance to harmful pests from all taxonomic groups of arthropods, especially to beetles (Coleoptera), two-winged insects (Diptera), and moths (Lepidoptera) and to nematodes (Nematoda). Genetically modified plants capable to synthesize one or more insecticidal proteins are, e.g., described in the citations mentioned above, some of which are commercially available such as YieldGard® (corn cultivars producing the Cry1Ab toxin), YieldGard® Plus (corn cultivars producing Cry1Ab and Cry3Bb1 toxins), Starlink® (corn cultivars producing the Cry9c toxin), Herculex® RW (corn cultivars producing Cry34Ab1, Cry35Ab1 and the enzyme Phosphinothricin-N-Acetyltransferase [PAT]); NuCOTN® 33B (cotton cultivars producing the Cry1Ac toxin), Bollgard® I (cotton cultivars producing the Cry1Ac toxin), Bollgard® II (cotton cultivars producing Cry1Ac and Cry2Ab2 toxins); VIPCOT® (cotton cultivars producing a VIP-toxin); NewLeaf® (potato cultivars producing the Cry3A toxin); Bt-Xtra®, NatureGard®, KnockOut®, BiteGard®, Protecta®, Bt11 (e.g., Agrisure® CB), and Bt176 from Syngenta Seeds SAS, France (corn cultivars producing the Cry1Ab toxin and PAT enzyme), MIR604 from Syngenta Seeds SAS, France (corn cultivars producing a modified version of the Cry3A toxin (see PCT Publication No. WO 03/018810 to Syngenta Participations AG, which is hereby incorporated by reference in its entirety), MON 863 from Monsanto Europe S.A., Belgium (corn cultivars producing the Cry3Bb1 toxin), IPC531 from Monsanto Europe S.A., Belgium (cotton cultivars producing a modified version of the Cry1Ac toxin), and 1507 from Pioneer Overseas Corporation, Belgium (corn cultivars producing the Cry1F toxin and PAT enzyme).

Plants also include those that, through the use of recombinant DNA techniques, are able to synthesize one or more proteins to increase the resistance or tolerance of those plants to bacterial, viral, or fungal pathogens. Non-limiting examples of such proteins are the so-called "pathogenesis-related proteins" ("PR" proteins, see e.g., European Patent No. 0392225 to Syngenta Participations AG, which is hereby incorporated by reference in its entirety), plant disease resistance genes (e.g., potato cultivars, which express resistance genes acting against *Phytophthora infestans* derived from the Mexican wild potato *Solanum bulbocastanum*) or T4-lysozyme (e.g., potato cultivars capable of synthesizing these proteins with increased resistance against bacteria such as *Erwinia amylovora*). The methods for producing such genetically modified plants are generally known to the person of ordinary skill in the art and are described, e.g., in the above-noted references.

Plants amenable to the method of the present invention also include those that through the use of recombinant DNA techniques are capable of synthesizing one or more proteins to increase the productivity (e.g., biomass production, grain yield, starch content, oil content, and/or protein content), tolerance to drought, salinity, or other growth-limiting environmental factors or tolerance to pests and fungal, bacterial, or viral pathogens of those plants.

Suitable plants also include those that through the use of recombinant DNA techniques contain a modified amount of substances of content or new substances of content, specifically to improve human or animal nutrition, e.g., oil crops that produce health-promoting long-chain omega-3 fatty acids or unsaturated omega-9 fatty acids (e.g., Nexera® rape, DOW Agro Sciences, Canada).

Suitable plants also include those that through the use of recombinant DNA techniques contain a modified amount of substances of content or new substances of content, specifically to improve raw material production, e.g., potatoes that produce increased amounts of amylopectin (e.g., Amflora® potato, BASF SE, Germany).

Particularly suited plants have been rendered tolerant to at least one herbicide, are resistant to glyphosate or an agriculturally acceptable salt thereof, and/or are resistant to dicamba or an agriculturally acceptable salt thereof.

The method of the present invention involves applying thiophanate methyl and an isolated hypersensitive response elicitor protein or polypeptide fragment to a plant and/or area of cultivation.

Thiophanate methyl is a fungicide which belongs to the functional class of benzimidazole precursor fungicides, or thiophanates. These fungicides act by disrupting β-tubulin assembly in mitosis. Based on the results in the accompanying examples, it is believed similar synergistic effects can be achieved with other members of this class of benzimidazoles.

Isolated HR elicitor proteins or polypeptide fragments are known in the art. In one embodiment, the isolated HR elicitor protein or polypeptide fragment is a full length HR elicitor protein, also known as harpin. Harpin includes any member of the art-recognized class of proteins that are produced by plant bacteria, and which share structural features and a capacity for inducing a plant hypersensitive response. Biochemically, these proteins or polypeptides have a number of common structural characteristics. These include being glycine rich, low or no cysteine content, heat stable, hydrophilic, lacking an N-terminal signal sequence, and susceptible to proteolysis. See Bonas, "Bacterial Home Goal by Harpins," *Trends Microbiol.* 2:1-2 (1994); Gopalan et al., "Bacterial Genes Involved in the Elicitation of Hypersensitive Response and Pathogenesis," *Plant Disease* 80:604-10 (1996); and Alfano et al., "The Type III (Hrp) Secretion Pathway of Plant Pathogenic Bacteria: Trafficking Harpins, Avr Proteins, and Death," *Journal of Bacteriology* 179:5655-5662 (1997), each of which is hereby incorporated by reference in its entirety. In addition, harpins share a unique secondary structure that has been associated with their distinct biological activities. The structure has two primary components, an alpha helix unit and a relaxed acidic unit having a sheet or random turn structure. In the absence of one or both of these components, hypersensitive response elicitation does not occur. See PCT Publication No. WO 01/98501 to Fan et al., which is hereby incorporated by reference in its entirety.

The harpin proteins also share the ability to induce specific plant responses (i.e., following their application to a plant and/or area of cultivation). The induction of plant disease resistance, plant growth, insect resistance, desiccation resistance, and post-harvest disease resistance (in harvested plant products, such as fruits and vegetables) are several of the more important utilities. These uses of the harpin proteins are described in U.S. Pat. No. 6,277,814 to Qiu et al.; U.S. Pat. No. 5,776,889 to Wei et al.; U.S. Pat. No. 5,977,060 to Zitter et al.; U.S. Pat. No. 6,235,974 to Qiu et al.; U.S. Patent Application Publication No. 2003/0104979 to Wei et al.; U.S. Patent Application Publication No. 2002/0019337 to Wei et al.; and U.S. Patent Application Publication No. 2004/0265442; each of which is hereby incorporated by reference in its entirety. The induction of these responses is due to upregulation of jasmonic acid/ethylene and salicylic acid defense pathways, as well as plant growth pathways that regulate photosynthesis and nutrient uptake.

One group of harpin proteins or polypeptides includes, without limitation, homologs of *Erwinia amylovora* HrpN, which include those from species of *Erwinia, Pantoea,* and *Pectobacterium*. Examples of such homologs include those harpin proteins identified at Genbank Accession Nos. AAC31644 (*Erwinia amylovora*); AAQ21220, AAQ17045, CAE25423, CAE25424, CAE25425, and CAF74881 (*Erwinia pyrifoliae*); CAC20124, Q47278, Q47279, and AAY17519 (*Erwinia chrysanthemi*); CAE25422 (*Erwinia* strain JP557); AAG01466 (*Pantoea stewartii*); AAF76342 (*Pantoea agglomerans*); ABZ05760, ABI15988, ABI15989, ABI15990, ABI15991, ABI15992, ABI15996, ABK80762, ABD04037, ABI15994, ABD04035, ABD04036, AAY17521, AAX38231, ABI15995, AAQ73910, and CAL69276 (*Pectobacterium carotovorum*); YP_050198, AAS20361, and CAE45180 (*Pectobacterium atrosepticum*); and ABD22989 (*Pectobacterium betavasculorum*), each of which is hereby incorporated by reference in its entirety.

Another group of harpin proteins or polypeptides includes, without limitation, homologs of *Erwinia amylovora* HrpW and *Pseudomonas syringae* HrpW, which includes those from species of *Erwinia, Pseudomonas, Xanthomonas, Acidovorax,* and *Pectobacterium*. Examples of such homologs include those harpin proteins identified at Genbank Accession Nos. U94513, CAA74158, AAC04849, and AAF63402 (*Erwinia amylovora*); AAQ17046 (*Erwinia pyrifoliae*); YP_001906489 (*Erwinia tasmaniensis*); YP_050207 (*Pectobacterium atrosepticum*); AF037983 (*Pseudomonas syringae* pv. tomato); AAO50075 (*Pseudomonas syringae* pv. *phaseolicola*); AAL84244 (*Pseudomonas syringae* pv. *maculicola*); AAX58537, AAX58557, AAX58525, AAX58531, AAX58527, AAX58577, AAX58491, AAX58515, AAX58517, AAX58523, AAX58583, AAX58451, AAX58561, AAX58453, AAX58541, AAX58589, AAT96311, AAX58497, AAX58579, AAX58449, AAX58485, AAX58563, AAX58581, AAX58575, AAX58569, AAX58567, AAX58505, AAX58591, AAX58503, AAX58507, AAX58509, AAX58469, AAX58441, AAX58543, AAX58495, AAX58549, AAX58593, AAX58511, AAX58519, AAT96270, AAX58447, AAX58571, AAX58465, AAX58489, AAX58533, AAX58535, AAX58461, AAT96350, AAX58473, AAX58483, AAX58475, AAX58457, AAX52461, AAX52457, AAT96222, (*Pseudomonas viridiflava*); ABA47299 and BAG24117 (*Pseudomonas cichorii*); CAH57075 (*Pseudomonas avellanae*); BAE80274 and BAE80242 (*Acidovorax avenae*); and AAM37767 (*Xanthomonas axonopodis* pv. *citri*), each of which is hereby incorporated by reference in its entirety.

Yet another group of harpin proteins or polypeptides includes, without limitation, homologs of *Pseudomonas syringae* HrpZ, which includes those from other species of *Pseudomonas*. Examples of such homologs include those harpin proteins identified at Genbank Accession Nos. P35674, AAB00127, ABL01505, AAQ92359, BAD20880, BAD20876, BAD20892, BAD20884, BAD20928, BAD20936, BAD20932, BAD20924, BAD20856, BAD20864, BAD20860, BAD20848, BAD20844, BAD20836, BAD20840, BAD20824, BAD20842, BAD20820, BAD20916, BAD20872, BAC81526, O87653, BAA74798, BAD20904, AAB86735, BAD20912, BAD20908, ABL01504, BAB40655, ABO26225, ABO26228 (*Pseudomonas syringae* pv.); BAD20868 (*Pseudomonas ficuserectae*); AAX52452, AAT96159, AAX52266, AAX52396, AAT96322, AAT96281, AAX52272, AAX52306, AAX52270, AAX52402, AAX52276, AAX52318, AAX52262, and AAT96361 (*Pseudomonas viridiflava*); CAJ76697 (*Pseudomonas avellanae*); YP_001185537 (*Pseudomonas mendocina*); and ABA47309 and BAG24128 (*Pseudomonas cichorii*), each of which is hereby incorporated by reference in its entirety.

An additional group of harpin proteins or polypeptides includes, without limitation, homologs of *Xanthomonas campestris* HreX (see U.S. Pat. No. 6,960,705 to Wei et al., which is hereby incorporated by reference in its entirety), which includes those from other species of *Xanthomonas*. Non-limiting examples of such homologs include those harpin proteins identified at Genbank Accession Nos. NP_636614, YP_001904470, YP_362171 (*Xanthomonas campestris*); ABB72197, ABK51585, ABU48601, ABK51584, YP_198734, and ZP_02245223 (*Xanthomonas oryzae*); and ABK51588 and NP_640771 (*Xanthomonas axonopodis*); each of which is hereby incorporated by reference in its entirety.

In another embodiment, the isolated HR elicitor protein or polypeptide fragment is a fragment or combination of fragments (i.e., a fusion protein) of one of the above referenced harpin proteins. In one embodiment, the fragment or fusion protein includes fragments that elicit the HR. In another embodiment, the fragment or fusion protein includes fragments that do not elicit the HR. Suitable fragments include, e.g., two structural units: a stable α-helix unit with 12 or more amino acids in length; and a hydrophilic, acidic unit with 12 or more amino acids in length, which could be a beta-form, a beta-turn, or unordered forms. Fragments may also be characterized by an acidic pI value that is preferably about 5 or below. Fragments may contain any number of amino acids, e.g., between about 25 and about 60, or between about 28 to about 40 amino acids.

Examples of suitable fragments are identified in U.S. Pat. No. 6,583,107 to Laby et al., and PCT Publication No. WO 01/098501 to Fan et al., each of which is hereby incorporated by reference in its entirety. PCT Publication No. WO 01/098501 to Fan et al. also describes methods for obtaining fragments of harpin protein or polypeptides that could be employed in the present invention.

Suitable HR-eliciting polypeptide fragments include, without limitation, those identified in Table 1.

TABLE 1

List of HR-Eliciting Fragments

| HR domain | Isolated Source | Amino Acid Residues | pI |
|---|---|---|---|
| HrpN$_{Ea}$-1 | E. amylovora | 43-70 | 3.09 |
| HrpN$_{Ea}$-2 | E. amylovora | 140-176 | 3.17 |
| HrpN$_{Ech}$-1 | E. chrysanthemi | 78-118 | 5.25 |
| HrpN$_{Ech}$-2 | E. chrysanthemi | 256-295 | 4.62 |
| HrpN$_{Ecc}$-1 | E. carotovora | 25-63 | 4.06 |
| HrpN$_{Ecc}$-2 | E. carotovora | 101-140 | 3.00 |
| HrpW$_{Pss}$-1 | P. syringae | 52-96 | 4.32 |
| HrpW$_{Ea}$-1 | E. amylovora | 10-59 | 4.53 |
| HrpZ$_{Pss}$-1 | P. syringae | 97-132 | 3.68 |
| HrpZ$_{Pss}$-2 | P. syringae | 153-189 | 3.67 |
| HrpZ$_{Pss}$-3 | P. syringae | 271-308 | 3.95 |
| PopA1$_{Rs}$-1 | R. solanacearum | 92-125 | 3.75 |
| PopA1$_{Rs}$-2 | R. solanacearum | 206-260 | 3.62 |

As noted above, suitable fragments of harpin protein or polypeptides may not elicit the hypersensitive response in plants, but may still be useful in the method and compositions of the present invention. Such fragments are described in U.S. Pat. No. 6,858,707 to Wei et al., which is hereby incorporated by reference in its entirety.

Examples of suitable fragments of a hypersensitive response elicitor which do not elicit a hypersensitive response include fragments of the *Erwinia amylovora* hypersensitive response elicitor are described in U.S. Pat. No. 6,858,707 to Wei et al., which is hereby incorporated by reference in its entirety. These include the C-terminal fragments of the HrpN amino acid sequence recited in U.S. Pat. No. 6,858,707 (which is hereby incorporated by reference in its entirety) that span the amino acids 169-403, 210-403, 267-403, or 343-403; and internal fragments of the HrpN amino acid sequence recited in U.S. Pat. No. 6,858,707 (which is hereby incorporated by reference in its entirety) that span the amino acids 150-179, 137-166, 121-150, 76-168, 105-168, or 137-156.

Another example of a useful fragment of a hypersensitive response elicitor which fragment does not itself elicit a hypersensitive response is the protein fragment containing amino acids 190 to 294 of the HrpZ amino acid sequence as recited in U.S. Pat. No. 6,858,707 (which is hereby incorporated by reference in its entirety).

Variants of fragments of hypersensitive response elicitors that do not elicit a hypersensitive response may be made by, for example, the deletion or addition of amino acids that have minimal influence on the properties, secondary structure, and hydropathic nature of the polypeptide. For example, a polypeptide may be conjugated to a signal (or leader) sequence at the N-terminal end of the protein which co-translationally or post-translationally directs transfer of the protein. The polypeptide may also be conjugated to a linker or other sequence for ease of synthesis, purification, or identification of the polypeptide.

Suitable fragments can be produced by several means. According to one approach, subclones of the gene encoding a known harpin protein or polypeptide are produced by conventional molecular genetic manipulation by subcloning gene fragments. The subclones then are expressed in vitro or in vivo in bacterial cells to yield a smaller protein or peptide that can be tested for activity.

As an alternative approach, fragments can be produced by digestion of a full-length harpin protein or polypeptide with proteolytic enzymes like chymotrypsin or *Staphylococcus* proteinase A, or trypsin. Different proteolytic enzymes are likely to cleave elicitor proteins at different sites based on the amino acid sequence of the harpin protein. Some of the fragments that result from proteolysis may be active elicitors.

In yet another approach, based on knowledge of the primary structure of the protein, fragments of the harpin protein gene may be synthesized by using the PCR technique together with specific sets of primers chosen to represent particular portions of the protein. These then would be cloned into an appropriate vector for expression of a truncated peptide or protein.

Chemical synthesis can also be used to make suitable fragments. Such a synthesis is carried out using known amino acid sequences for the harpin being produced. Alternatively, subjecting a full length harpin to high temperatures and pressures will produce fragments. These fragments can then be separated by conventional procedures (e.g., chromatography, SDS-PAGE).

Harpin protein or polypeptides of the present invention may also include isolated hypersensitive response elicitor fusion proteins comprising two or more spaced apart HR-eliciting or non-eliciting domains.

Building blocks containing one or more HR-eliciting domains include, without limitation, the building blocks identified in Table 2.

TABLE 2

Building Block Domains for Fusion Proteins

| Domain Sequence | Source | MW (kDa) | #a.a. | pI |
|---|---|---|---|---|
| A | PopA70-146 | 10.69 | 104 | 6.48 |
| (N$_N$) | HrpN$_{Ea}$40-80 | 6.754 | 68 | 6.78 |
| (N$_N$)$_2$ | Dimer of HrpN$_{Ea}$40-80 | 10.84 | 111 | 6.13 |
| (N$_N$)$_3$ | Triplemer of HrpN$_{Ea}$40-80 | 14.93 | 154 | 5.63 |
| (N$_N$)$_4$ | Tetramer of HrpN$_{Ea}$40-80 | 19.01 | 197 | 4.95 |
| (N$_C$) | HrpN$_{Ea}$140-180 | 7.224 | 68 | 5.01 |
| (N$_C$)$_2$ | Dimer of HrpN$_{Ea}$140-180 | 11.78 | 111 | 3.98 |
| (N$_C$)$_3$ | Trimer of HrpN$_{Ea}$140-180 | 16.34 | 154 | 3.72 |
| (N$_C$)$_4$ | Tetramer of HrpN$_{Ea}$140-180 | 20.89 | 197 | 3.58 |
| (N$_C$)$_{10}$ | Decamer of HrpN$_{Ea}$140-180 | 48.23 | 455 | 3.28 |
| (N$_C$)$_{16}$ | Hexadecamer of HrpN$_{Ea}$140-180 | 75.57 | 713 | 3.18 |
| W | HrpW$_{Ea}$10-59 | 7.986 | 77 | 6.48 |
| Z$_N$ | HrpZ90-150 | 8.087 | 78 | 5.38 |
| Z$_{266-308}$ | HrpZ266-308 | 7.029 | 70 | 6.40 |

With the combination of these (and other) HR-eliciting domains, fusion proteins can be produced that have higher HR potency and have enhanced ability to induce desired plant response, in this case increased yield, and enhanced growth. These fusion proteins can be formed using one HR domain repeat unit (concatemer), different combinations of HR domains, and/or biologically active domains from other elicitors.

Using these building blocks, several isolated fusion proteins include, without limitation, those identified in Table 3.

TABLE 3

Fusion Protein Constructions

| Protein | Domain Sequence | MW (kDa) | # a.a. | pI |
|---|---|---|---|---|
| SH-1 | *W(N$_N$)$_4$A(N$_C$)$_4$Z$_{266-308}$ | 54.955 | 545 | 3.69 |
| SH-2 | *W(N$_N$)$_4$Z$_N$(N$_C$)$_4$Z$_{266-308}$ | 52.341 | 519 | 3.54 |
| SH-3 | *W(N$_N$)$_4$Z$_N$(N$_C$)$_4$Z$_{266-308}$A | 60.375 | 598 | 3.67 |

These fusion proteins are heat stable and soluble, and have been demonstrated to possess improved growth enhancement activity as compared to harpin proteins isolated from plant pathogenic bacteria, such as HrpN. These fusion proteins are described in PCT Publication No. WO 01/098501 to Fan et al., which is hereby incorporated by reference in its entirety.

One preferred fusion protein, now commercially available from Plant Health Care Inc., is characterized by the amino acid sequence of SEQ ID NO:1 as follows:

```
MSLNTSGLGA STMQISIGGA GGNNGLLGTH MPGTSSSPGL

FQSGGDNGLG GHNANSALGQ QPIDRQTIEQ MAQLLAELLK

SLLDSGEKLG DNFGASADSA SGTGQQDLMT QVLNGLAKSM

LDDLLTKQDG GTSFSEDDSG PAKDGNANAG ANDPSKNDPS

KSQGPQSANK TGNVDDANNQ DPMQALMQLL EDLVKLLKAA

LHMQQPGGND KGNGVGGDSG QNDDSTSGTD STSDSSDPMQ

QLLKMFSEIM QSLFGDEQDG TDSTSGSRFT RTGIGMKAGI

QALNDIGTHS DSSTRSFVNK GDRAMAKEIG QFMDQYPEVF

GKPQYQKGPG QEVKTDDKSW AKALSKPDDD GMTPASMEQF

NKAKGMIKSA MAGDTGNGNL QARGAGGSSL GIDAMMAGDA

INNMALGKLG AA
```

Residues 1-30 of SEQ ID NO:1 correspond to the N-terminal sequence of HrpN$_{Ea}$; residues 31-34 (bold) are artifacts of ligating the HR domains together; residues 35-83 correspond to one HR domain of HrpW$_{Ea}$ (residues 10-59); residues 84-86 (bold) are artifacts of ligating the HR domains together; residues 87-138 correspond to one HR domain of HrpZ$_{Pss}$ (residues 90-141); residues 139-140 (bold) are artifacts of ligating the HR domains together; residues 141-211 correspond to one HR domain of PopA (residues 70-140); residues 212-220 correspond to artifacts of ligating the HR domains together; residues 221-261 correspond to one HR domain of HrpN$_{Ea}$ (residues 140-180); residues 262-271 correspond to artifacts of ligating the HR domains together; and residues 272-412 correspond to the C-terminal sequence of HrpN$_{Ea}$ (residues 263-403).

The fusion protein of SEQ ID NO:1 is encoded by the nucleotide sequence of SEQ ID NO:2 as follows:

```
ATGAGTCTGA ATACAAGTGG GCTGGGAGCG TCAACGATGC

AAATTTCTAT CGGCGGTGCG GGCGGAAATA ACGGGTTGCT

GGGTACGCAT ATGCCCGGGA CCTCGTCCTC GCCGGGTCTG

TTCCAGTCCG GGGGGGACAA CGGGCTTGGT GGTCATAATG

CAAATTCTGC GTTGGGGCAA CAACCCATCG ATCGGCAAAC

CATTGAGCAA ATGGCTCAAT TATTGGCGGA ACTGTTAAAG

TCACTGCTAG ATAGTGGGGA AAAGCTCGGT GACAACTTCG

GCGCGTCTGC GGACAGCGCC TCGGGTACCG GACAGCAGGA

CCTGATGACT CAGGTGCTCA ATGGCCTGGC CAAGTCGATG

CTCGATGATC TTCTGACCAA GCAGGATGGC GGGACCAGCT

TCTCCGAAGA CGATAGTGGG CCGGCGAAGG ACGGCAATGC

CAACGCGGGC GCCAACGACC CGAGCAAGAA CGACCCGAGC

AAGAGCCAGG GTCCGCAGTC GGCCAACAAG ACCGGCAACG

TCGACGACGC CAACAACCAG GATCCGATGC AAGCGCTGAT
```

-continued

```
GCAGCTGCTG GAAGACCTGG TGAAGCTGCT GAAGGCGGCC

CTGCACATGC AGCAGCCCGG CGGCAATGAC AAGGGCAACG

GCGTGGGCGG TGATAGTGGG CAAAACGACG ATTCCACCTC

CGGCACAGAT TCCACCTCAG ACTCCAGCGA CCCGATGCAG

CAGCTGCTGA AGATGTTCAG CGAGATAATG CAAAGCCTGT

TTGGTGATGA GCAAGATGGC ACCGATAGTA CTAGCGGCTC

GAGGTTTACT CGTACCGGTA TCGGTATGAA AGCGGGCATT

CAGGCGCTGA ATGATATCGG TACGCACAGC GACAGTTCAA

CCCGTTCTTT CGTCAATAAA GGCGATCGGG CGATGGCGAA

GGAAATCGGT CAGTTCATGG ACCAGTATCC TGAGGTGTTT

GGCAAGCCGC AGTACCAGAA AGGCCCGGGT CAGGAGGTGA

AAACCGATGA CAAATCATGG GCAAAAGCAC TGAGCAAGCC

AGATGACGAC GGAATGACAC CAGCCAGTAT GGAGCAGTTC

AACAAAGCCA AGGGCATGAT CAAAAGCGCC ATGGCGGGTG

ATACCGGCAA CGGCAACCTG CAGGCACGCG GTGCCGGTGG

TTCTTCGCTG GGTATTGATG CCATGATGGC CGGTGATGCC

ATTAACAATA TGGCACTTGG CAAGCTGGGC GCGGCTTAA
```

In carrying out the method of the present invention, application of the fungicide thiophanate methyl and the isolated hypersensitive response elicitor protein or polypeptide fragment may occur by either applying to the plant and/or area of cultivation each compound in sequence or by applying a single composition containing both compounds. Either way, the application of both compounds (either sequentially or simultaneously) is carried out to synergistically increase yield of the plant.

In one embodiment, application is carried out by applying a formulation of thiophanate methyl and a formulation of an isolated hypersensitive response elicitor protein or polypeptide fragment, either at the same time (e.g., combined into a single formulation mixture, or applied simultaneously as two individual formulations) or in succession to achieve substantially the same result.

Application in succession means thiophanate methyl is applied before or after an isolated HR elicitor protein or polypeptide fragment. When application of the two compounds occurs successively, the time interval between the individual applications is selected to ensure that the active substance applied first still occurs at the site of action in a sufficient amount at the time of application of the further active substance(s). Preferably, the time interval for a subsequent application of an active compound (and any additional compounds) ranges from about a few seconds up to about 3 months, or about 1, 2, 3, 4, 5, 6, 7, 8, 9, or about 10 seconds, 1 minute, about 1-3, 5, 10, 15, 30, or 45 minutes, about 1 hour, 2-3 hours, 5 hours, 10 hours, 15 hours, 20 hours, or 24 hours, about 1-3 days, 5 days, 1 week, 2 weeks, 3 weeks, 4 weeks, 1 month, or about 1-5 months.

The order of application of the two substances is not essential for operation of the present invention. Furthermore, as discussed more fully below, application of one or both of these substances or their combination, can be repeated one or more times during the growing season.

Thiophanate methyl and isolated HR elicitor protein or polypeptide fragments may be formulated into two separate formulations or compositions, or a single formulation or composition.

Agricultural formulations of active substances are well known. Non-limiting examples include solutions, emulsions, suspensions, dusts, powders, pastes, and granules. The particular formulation chosen may vary depending on the particular intended application. In each case, it is typically advantages to ensure a fine and even distribution of the active ingredient(s) in a liquid or solid carrier.

Formulation methods are taught, e.g., in U.S. Pat. No. 3,060,084 to Littler and European Patent No. 0707445 to BASF AG (for liquid concentrates); Browning, "Agglomeration," *Chemical Engineering* pp. 147-48 (1967); *Perry's Chemical Engineer's Handbook*, 4th Ed., McGraw-Hill, New York, 1963; PCT Publication No. WO 91/13546 to E.I. Du Pont De Nemours and Co.; U.S. Pat. No. 4,172,714 to Albert; U.S. Pat. No. 4,144,050 to Frensch et al.; U.S. Pat. No. 3,920,442 to Albert; U.S. Pat. No. 5,180,587 to Moore; U.S. Pat. No. 5,232,701 to Ogawa et al.; U.S. Pat. No. 5,208,030 to Hoy et al., Great Britain Patent No. 2,095,558; U.S. Pat. No. 3,299,566 to Macmullen; Klingman, *Weed Control as a Science*, J. Wiley & Sons, New York, 1961; Hance et al., *Weed Control Handbook*, 8th Ed., Blackwell Scientific, Oxford, 1989; and Mollet and Grubemann, *Formulation Technology*, Wiley VCH Verlag, Weinheim, 2001, each of which is hereby incorporated by reference in its entirety.

Thiophanate methyl and isolated HR elicitor protein or polypeptide fragments may be formulated (either together or separately) in a manner common for agrochemical formulations. For example, the composition(s) may include auxiliaries which are customary in agrochemical formulations. The particular auxiliaries used may depend on the particular application form and active substance, respectively. Non-limiting examples of suitable auxiliaries include solvents, solid carriers, dispersants, or emulsifiers (e.g., further solubilizers, protective colloids, surfactants, and adhesion agents), organic and inorganic thickeners, bactericides, anti-freezing agents, anti-foaming agents, colorants, tackifiers or binders, or combinations thereof.

Suitable solvents include water; organic solvents such as mineral oil fractions of medium to high boiling point, coal tar oils and oils of vegetable or animal origin; aliphatic, cyclic and aromatic hydrocarbons (e.g., toluene, xylene, paraffin, tetrahydronaphthalene, alkylated naphthalenes, or their derivatives); alcohols such as methanol, ethanol, propanol, butanol, and cyclohexanol; glycols; ketones such as cyclohexanone and gamma-butyrolactone; fatty acid dimethylamides; fatty acids and fatty acid esters; and strongly polar solvents (e.g., amines such as N-methylpyrrolidone).

Suitable solid carriers include mineral earths such as silicates, silica gels, talc, kaolins, limestone, lime, chalk, bole, loess, clays, dolomite, diatomaceous earth, calcium sulfate, magnesium sulfate, magnesium oxide, ground synthetic materials, fertilizers (e.g., ammonium sulfate, ammonium phosphate, ammonium nitrate, ureas, and products of vegetable origin, such as cereal meal, tree bark meal, wood meal and nutshell meal); cellulose powders; and other solid carriers.

Suitable surfactants (also known as adjuvants, wetters, tackifiers, dispersants, or emulsifiers) are alkali metal, alkaline earth metal, and ammonium salts of aromatic sulfonic acids (e.g., ligninsulfonic acid (Borresperse® types, Borregard, Norway)) phenolsulfonic acid, naphthalenesulfonic acid (Morwet® types, Akzo Nobel, U.S.A.), dibutylnaphthalene-sulfonic acid (Nekal® types, BASF, Germany), fatty acids, alkylsulfonates, alkylarylsulfonates, alkyl sulfates, laurylether sulfates, fatty alcohol sulfates, sulfated hexa-, hepta- and octadecanolates, sulfated fatty alcohol glycol ethers, condensates of naphthalene or of naphthalenesulfonic acid with phenol and formal-dehyde, polyoxy-ethylene octylphenyl ether, ethoxylated isooctylphenol, octylphenol, nonylphenol, alkylphenyl polyglycol ethers, tributylphenyl polyglycol ether, tristearyl-phenyl polyglycol ether, alkylaryl polyether alcohols, alcohol and fatty alcohol/ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquid and proteins, denatured proteins, polysaccharides (e.g., methylcellulose), hydrophobically modified starches, polyvinyl alcohols (Mowiol® types, Clariant, Switzerland), polycarboxylates (Sokolan® types, BASF, Germany), polyalkoxylates, polyvinylamines (Lupasol® types, BASF, Germany), polyvinylpyrrolidone and copolymers thereof.

Examples of thickeners (i.e., compounds that impart a modified flowability to formulations (i.e., high viscosity under static conditions and low viscosity during agitation) are polysaccharides and organic and inorganic clays such as Xanthan gum (Kelzan®, CP Kelco, U.S.A.), Rhodopol® 23 (Rhodia, France), Veegum® (R.T. Vanderbilt, U.S.A.) or Attaclay® (Engelhard Corp., NJ, USA).

Bactericides may be added to the composition for preservation and stabilization. Examples of suitable bactericides include, e.g., those based on dichlorophene and benzylalcohol hemi formal (Proxel® from ICI, Acticide® RS from Thor Chemie, and Kathon® MK from Rohm & Haas) and isothiazolinone derivatives such as alkylisothiazolinones and benzisothiazolinones (Acticide® MBS from Thor Chemie).

Examples of suitable anti-freezing agents are ethylene glycol, propylene glycol, urea, and glycerin.

Examples of anti-foaming agents are silicone emulsions (e.g., Silikon® SRE, Wacker, Germany and Rhodorsil®, Rhodia, France), long chain alcohols, fatty acids, salts of fatty acids, fluoroorganic compounds, and mixtures thereof.

Suitable colorants are pigments of low water solubility and water-soluble dyes. Non-limiting examples include rhodamin B, C. I. pigment red 112, C. I. solvent red 1, pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, and basic red 108.

Examples of tackifiers or binders include polyvinylpyrrolidones, polyvinylacetates, polyvinyl alcohols, and cellulose ethers (e.g., Tylose®, Shin-Etsu, Japan).

Powders, materials for spreading, and dusts can be prepared by mixing or concomitantly grinding the active compounds with at least one solid carrier.

Granules (e.g., coated granules, impregnated granules, and homogeneous granules) can be prepared by binding the active substances to solid carriers. Examples of solid carriers are mineral earths such as silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers (e.g., ammonium sulfate, ammonium phosphate, ammonium nitrate, ureas, and products of vegetable origin, such as cereal meal, tree bark meal, wood meal and nutshell meal), cellulose powders, and other solid carriers.

In one embodiment, the composition is formulated for dilution with water. Thus, the composition may be formulated as a water soluble concentrate, a dispersable concentrate, an emulsifiable concentrate, an emulsion, a suspension, water-dispersible granules and/or water-soluble granules, water-dispersible powders and/or water-soluble powders, or a gel.

In the case of water-soluble concentrates, the formulation may include e.g., about 10 parts by weight of the composition of the present invention dissolved in about 90 parts by weight of water or a water-soluble solvent. As an alternative, wetting agents or other auxiliaries may be added. The active substances dissolve upon dilution with water. In this way, a formulation having a content of about 10% by weight of active substance is obtained.

In the case of dispersible concentrates, the formulation may include, e.g., about 20 parts by weight of the active compound(s) dissolved in about 70 parts by weight of cyclohexanone with addition of about 10 parts by weight of a dispersant, e.g., polyvinylpyrrolidone. Dilution with water gives a dispersion. According to this formulation, the active substance content is about 20% by weight.

In the case of emulsifiable concentrates, the formulation may include, e.g., about 15 parts by weight of the active compound(s) dissolved in about 75 parts by weight of xylene with addition of calcium dodecylbenzenesulfonate and castor oil ethoxylate (in each case about 5 parts by weight). Dilution with water gives an emulsion. The composition has an active substance content of about 15% by weight.

In the case of an emulsion, the formulation may include, e.g., about 25 parts by weight of active compound(s) dissolved in about 35 parts by weight of xylene with addition of calcium dodecylbenzenesulfonate and castor oil ethoxylate (in each case about 5 parts by weight). This mixture is introduced into about 30 parts by weight of water by means of an emulsifying machine (Ultraturrax) and made into a homogeneous emulsion. Dilution with water gives an emulsion. The composition has an active substance content of about 25% by weight.

In the case of a suspension, in an agitated ball mill about 20 parts by weight of the active compound(s) comminuted with an addition of about 10 parts by weight of dispersants and wetting agents and about 70 parts by weight of water or an organic solvent to give a fine active substance suspension. Dilution with water gives a stable suspension of the active substance. The active compound(s) in the composition is about 20% by weight.

In the case of water-dispersible granules and/or water-soluble granules, the formulation may include, e.g., about 50 parts by weight of the active compound(s) ground finely with about 50 parts by weight of dispersants and wetting agents and prepared as water-dispersible or water-soluble granules by means of technical appliances (e.g., extrusion, spray tower, fluidized bed). Dilution with water gives a stable dispersion or solution of the active substance. The composition has an active compound(s) content of about 50% by weight.

In the case of water-dispersible powders and/or water-soluble powders, the formulation may include, e.g., about 75 parts by weight of the active compound(s) ground in a rotor-stator mill with addition of about 25 parts by weight of dispersants, wetting agents, and silica gel. Dilution with water gives a stable dispersion or solution of the active substances. The active compound(s) content of the composition is about 75% by weight.

In the case of a gel, the formulation may include, e.g., about 20 parts by weight of the active compound(s) agitated in a ball mill and comminuted with the addition of about 10 parts by weight of dispersants, about 1 part by weight of a gelling agent, and about 70 parts by weight of water or an organic solvent to give a fine suspension of the active substances. Dilution with water gives a stable suspension of the active substances, whereby a composition with about 20% (w/w) of active compound(s) is obtained.

In another embodiment, the active compound(s) is formulated for an undiluted application. Thus, the active compound(s) may be formulated as a dustable powder, granules, or Ultra Low Volume ("ULV") (e.g., fogging) solutions.

In the case of a dustable powder, the formulation may include, e.g., about 5 parts by weight of active compound(s) ground finely and mixed intimately with about 95 parts by weight of finely divided kaolin. This gives a dustable composition having an active substance content of about 5% by weight.

In the case of granules, the formulation may include, e.g., about 0.5 parts by weight of the active compound(s) ground finely and associated with about 99.5 parts by weight of carriers. This gives granules to be applied undiluted having an active compound(s) content of about 0.5% by weight.

In the case of ULV solutions, the formulation may include, e.g., about 10 parts by weight of the active compound(s) dissolved in about 90 parts by weight of an organic solvent, e.g., xylene. This gives a composition to be applied undiluted having an active compound(s) content of about 10% by weight.

In the present invention, agrochemical formulations generally comprise between about 0.01% and about 95%, or between about 0.1% and about 90%, or between about 0.5% and about 90%, by weight of active substances.

In one embodiment, the active compound(s) have a purity of from about 90% to 100%, or from about 95% to 100% (according to NMR spectrum).

As it pertains particularly to formulations of isolated HR elicitor protein or polypeptide fragments, stable liquid compositions containing a harpin protein or polypeptide may involve obtaining a liquid extract that is substantially free of cellular debris. In one embodiment, this is accomplished by fermenting a suspension of harpin protein or polypeptide-producing plant bacteria. Harpin protein or polypeptides can be produced readily through fermentation in rapidly growing bacteria. For example, recombinant *Escherichia coli* may be used for large-scale harpin protein or polypeptide production. Current technology enables the production of relatively large intracellular concentrations of harpin proteins or polypeptides.

Recombinant methodologies generally involve inserting a DNA molecule expressing a protein or polypeptide of interest into an expression system to which the DNA molecule is heterologous (i.e., not normally present). The heterologous DNA molecule is inserted into the expression system or vector in proper sense orientation and correct reading frame. The vector contains the necessary elements for the transcription and translation of the inserted protein-coding sequences. Transcription of DNA is dependent upon the presence of a promoter. Similarly, translation of mRNA in prokaryotes depends upon the presence of the proper prokaryotic signals which differ from those of eukaryotes. For a review on maximizing gene expression, see Roberts and Lauer, *Methods in Enzymology* 68:473 (1979), which is hereby incorporated by reference.

Regardless of the specific regulatory sequences employed, the DNA molecule is cloned into the vector using standard cloning procedures in the art, as described by Sambrook et al., *Molecular Cloning: A Laboratory Manual, Cold Springs Laboratory*, Cold Springs Harbor, N.Y. (1989), which is hereby incorporated by reference in its entirety. Once the isolated DNA molecule encoding the harpin protein or polypeptide has been cloned into an expression system, it is ready to be incorporated into a host cell. Such incorporation can be carried out by the various forms of transformation, depending upon the vector/host cell system. Suitable host cells include, but are not limited to, bacteria, virus, yeast, mammalian cells, insect, plant, and the like.

Optionally, the recombinant host cells can be host cells that express a native or recombinant, functional type III secretion system. This is described in detail in U.S. Pat. No. 6,596,509 to Bauer et al., which is hereby incorporated by reference in its entirety. As a consequence of expressing the functional type III secretion system, the cells will express the harpin protein or polypeptide and then secrete the protein into the culture medium. This can simplify isolation and purification of the harpin protein or polypeptide.

The recombinant host cells can be grown in appropriate fermentation chambers, preferably under temperature and nutrient conditions that optimize growth of the host cells and the expression of the harpin proteins or polypeptides. Persons of skill in the art are fully able to identify optimal conditions for particular host cells.

After fermentation, the bacterial suspension may be diluted in, e.g., about 2 to 5 fold volume of a buffer to adjust the pH between about 5.5 to 10, more preferably to a pH of between about 7 to 9, and even more preferably to a pH of about 8.0. Suitable buffers are well-known in the art and may include, for example, potassium phosphate buffer or a Tris-EDTA buffer. The concentration of the buffer can be from about 0.001 mM to about 0.5 M.

Following the pH adjustment, the bacterial suspension solution is heat treated to a temperature of about 60-130° C., preferably to a temperature of about 95-125° C. Heat treatment may be carried out for any suitable period of time. In one embodiment, heat treatment is carried out for a period of about five minutes up to about 30 minutes.

The heated suspension solution is then cooled. A suitable cool down temperature is, without limitation, about 35-55° C., preferably about 45° C.

Following cooling, bacterial cells in the bacterial suspension are lysed, if required, to liberate the harpin protein or polypeptide. Cell lysis may be carried out, e.g., by contacting the bacterial suspension with a lysozyme. The concentration of lysozyme may be anywhere from about 2 ppm to 100 ppm. Alternatively, cell lysis may involve non-chemical methods, such as high pressure or sonication, both of which are well known by persons of ordinary skill in the art.

It may be desirable, after cell lysis, to incubate the bacterial suspension. Suitable incubation times may vary. For example, it may be desirable to incubate the bacterial suspension for a period of about 30-45 minutes at a temperature of about 40-42° C.

After lysing, the desired protein or polypeptide (i.e., harpin protein or polypeptide, or fragment thereof) can be further extracted by removing the cell debris and the denatured proteins resulting from the previous heat treatment step. In one embodiment, the extract is centrifuged for about 10-20 minutes to remove some of the cell debris. Suitable centrifuge speeds may be from about 4,000 to 20,000 rpm and the spinning down time can be from about 10 minutes to 20 minutes. Further cell debris may then be removed by heat treating and centrifuging the supernatant to obtain a liquid extract that is substantially free of cellular debris by removing more than about 60%, 70%, 80%, 90%, or 95% of total solids. This subsequent heat treatment may be carried out at a temperature of about 60° C. for up to about two hours, at about 100° C. for about 10 minutes, or at about 121° C. with 15 psi of pressure for about 5 minutes. These temperatures and times may vary depending on other conditions.

A stable liquid composition containing a harpin protein or polypeptide may further involve introducing into the liquid extract a biocidal agent and, optionally, one or both of a protease inhibitor and a non-ionic surfactant, thereby obtaining a liquid composition comprising the isolated harpin protein or polypeptide fragment. In one embodiment, a protease inhibitor is introduced into the liquid extract without a non-ionic surfactant. In another embodiment, a non-ionic surfactant is introduced into the liquid extract without a protease inhibitor. In a further embodiment, both a protease inhibitor and a non-ionic surfactant are introduced into the liquid extract. In yet another embodiment, neither a protease inhibitor nor a non-ionic surfactant are introduced into the liquid extract.

Biocidal agents are added to the liquid extract for preservation. Suitable biocidal agents include, without limitation, antibiotics, toxic chemicals, and disinfectants. For example, a suitable antibiotic is streptomycin, a suitable toxic agent is sodium azide, and a suitable disinfectant is a Triple Action disinfectant (i.e., the EPA approved pesticide with the following active ingredients: 1-decanaminium, N,N-dimethyl-N-octyl-, chloride (12.4% by mass); 1-octanaminium, N,N-dimethyl-N-octyl-, chloride (12.4% by mass); alkyl(C12-16) dimethylbenzylammonium chloride (12.4% by mass); sodium carbonate (3% by mass); and edentate sodium (2.5% by mass)). The concentration of biocidal agent introduced may be in the range of about 1 ppm to about 100 ppm, more preferably about 2 ppm to about 30 ppm, most preferably about 5 ppm to about 10 ppm.

Protease inhibitors may be added to prevent harpin degradation by residual proteases in the harpin extract. Protease inhibitors include various inhibitors classed by protease type or by their mechanism of action. Suitable protease inhibitors may include, without limitation, cysteine protease inhibitors, serine protease inhibitors (serpins), trypsin inhibitors, threonine protease inhibitors, aspartic acid protease inhibitors, and metalloprotease inhibitors. Suitable protease inhibitors may be selected according to their mechanism of action. For example, suitable protease inhibitors may include, without limitation, suicide inhibitors, transition state inhibitors, protein protease inhibitors, and chelating agents. Examples of commercially available protease inhibitors include, without limitation, aprotinin, bestatin, calpain inhibitor I, calpain inhibitor II, chymostatin, E-64, leupeptin (N-acetyl-L-leucyl-L-leucyl-L-argininal), alpha-2-macroglobuline, pefabloc SC, pepstatin, PMSF (phenylmethanesulfonyl fluoride), and tosyl-L-lysine chloromethyl ketone (TLCK).

Protease inhibitors may be added to the extract at a concentration of about 1 ppm to about 100 ppm, more preferably about 2 ppm to about 30 ppm, most preferably about 5 ppm to about 10 ppm.

Suitable non-ionic surfactants include, without limitation, sorbitan fatty acid ester, glycerin fatty acid ester, fatty acid polyglyceride, fatty acid alcohol polyglycol ether, acetylene glycol, acetylene alcohol, oxyalkylene block polymer, polyoxyethylene alkyl ether, polyoxyethylene alkylaryl ether, polyoxyethylene styrylaryl ether, polyoxyethylene glycol alkyl ether, polyoxyethylene fatty acid ester, polyoxyethylene sorbitan fatty acid ester, polyoxyethylene glycerin fatty acid ester, polyoxyethylene hydrogenated castor oil, and polyoxypropylene fatty acid ester.

Non-ionic surfactants may be added to the extract at a volume amount of about 0.005 to about 20%, more preferably about 0.01 to about 15%, most preferably about 0.05% to about 10%.

As a result of introducing the biocidal agent and, optionally, the protease inhibitor and surfactant as described above, the composition can maintain its harpin activity for at least 72 hours and preferably much longer. Preferably, the composition retains harpin activity for more than about 5 days, 1 week, 2 weeks, 3 weeks, or 4 weeks, more preferably at least about 2 to 3 months, and most preferably longer than about 4 to 6 months. As used herein, retention of harpin activity can be determined by comparing the activity of the aged liquid composition to a recently prepared liquid composition or to a prior assessment made on the same composition. The activity can be measured by the effects of the composition on plants as assessed by the disease resistance, growth enhancement, stress resistance, etc., of the plants following challenge. Preferably, the compositions of the present invention retain (for more than 72 hours) at least about 70% activity, more preferably at least about 70% to about 80% activity, and most preferably at least about 80% to 90% activity.

Active substances of the composition of the present invention (i.e., at least thiophanate methyl and an isolated hypersensitive response elicitor protein or polypeptide fragment) can be applied alone and in sequence, or as a single composition, e.g., in the form of directly sprayable solutions, powders, suspensions, dispersions, emulsions, oil dispersions, pastes, dustable products, materials for spreading, or granules, by means of spraying, atomizing, dusting, spreading, brushing, immersing, or pouring. The application form depends on the intended purpose to ensure in each case the finest possible distribution of the active compound(s).

Aqueous application forms can be prepared from emulsion concentrates, pastes, or wettable powders (e.g., sprayable powders and oil dispersions) by adding water. To prepare emulsions, pastes, or oil dispersions, the substances (i.e., active compounds), as such or dissolved in an oil or solvent, can be homogenized in water by means of a wetter, tackifier, dispersant, or emulsifier. Alternatively, it is possible to prepare concentrates composed of an active substance, wetter, tackifier, dispersant, or emulsifier and, if appropriate, solvent or oil, and such concentrates are suitable for dilution with water.

The weight ratio of the individual compounds to the total composition will depend on the properties of the individual compounds (e.g., the specific isolated hypersensitive response elicitor protein or polypeptide fragment, and/or the presence of other compounds). The active substance concentrations in the ready-to-use formulations can be varied within relatively wide ranges. In general, they are from about 0.0001% to about 10%, or from about 0.001% to about 1% by weight. The compositions may also be used successfully in the ultra-low-volume process (ULV), it being possible to apply compositions comprising over 95% by weight of active substances, or even to apply the active substances without additives.

Various types of oils, wetters, adjuvants, herbicides, fungicides, other pesticides, or bactericides may be added to the agricultural compositions and, if appropriate, not until immediately prior to use (e.g., tank mix). These agents can be admixed with the active compounds in a weight ratio of about 1:100 to about 100:1, or about 1:10 to about 10:1. Individual pesticide components may be generally known by persons of ordinary skill in the art, such as those described in *The Pesticide Manual, 15th Edition*, British Crop Protection Council (2009), which is hereby incorporated by reference in its entirety.

The formulations may also contain fertilizers, such as ammonium nitrate, urea, potash, superphosphate, phytotoxicants, plant growth regulators, and safeners. Fertilizers may be applied separately from the formulations of the active substances or may be included in the compositions, e.g., by being added immediately prior to use (tank mix). In one embodiment, a plant and/or area of cultivation may be sprayed with a composition of the present invention either before or after the same is treated with a fertilizer.

In one embodiment, the composition includes thiophanate methyl and is applied to a plant and/or area of cultivation at an amount of between about 1 fl oz/acre to about 200 fl oz/acre of thiophanate methyl, or between about 5 fl oz/acre and about 100 fl oz/acre of thiophanate methyl, or between about 10 fl oz/acre and about 50 fl oz/acre of thiophanate methyl, or between about 15 fl oz/acre to about 30 fl oz/acre of thiophanate methyl.

In another embodiment, the composition includes an isolated hypersensitive response elicitor protein or polypeptide fragment and is applied to a plant and/or area of cultivation at an amount of between about 0.25 dry oz/acre and about 15 dry oz/acre of the isolated hypersensitive response elicitor protein or polypeptide fragment, or between about 0.5 dry oz/acre and about 10 dry oz/acre of the isolated hypersensitive response elicitor protein or polypeptide fragment, or between about 0.75 dry oz/acre and about 5 dry oz/acre of the isolated hypersensitive response elicitor protein or polypeptide fragment, or between about 1 dry oz/acre to about 2.5 dry oz/acre of the isolated hypersensitive response elicitor protein or polypeptide fragment.

Active compounds in the formulations may have different crystal modifications to alter biological activity. In all ternary and quaternary compositions used, compounds are present in amounts which result in a synergistic plant health increasing effect.

Further active compounds, e.g., insecticides, herbicides, fungicides, and/or herbicidal or growth-regulating compounds or fertilizers can then be added as further active components according to need. In one embodiment, formulations of the present invention may include one or more additional active ingredients selected from the group of glyphosate, dicamba, and glufosinate. In this embodiment, the plants are resistant to these herbicides.

Glyphosate and dicamba can also be used as their agriculturally acceptable salts and esters. Suitable salts of glyphosate include those salts of glyphosate where the counterion is an agriculturally acceptable cation. Suitable non-limiting examples of such salts are glyphosate-ammonium, glyphosate-diammonium, glyphosate-dimethylammonium, glyphosate-isopropylammonium, glyphosate-potassium, glyphosate-sodium, glyphosate-sesquisodium, glyphosate-sesquipotassium, glyphosate-trimethylsulphonium (sulphosate), glyphosate-trimesium, as well as the ethanolamine and diethanolamine salts. In one embodiment, the salt of glyphosate is selected from glyphosate-diammonium, glyphosate-isopropylammonium, glyphosate-sesquisodium, and glyphosata-trimethylsulphonium (sulphosate).

Suitable salts of dicamba include those salts of dicamba where the counterion is an agriculturally acceptable cation. Suitable examples of such salts are dicamba-sodium, dicamba-potassium, dicamba-methylammonium, dicamba-dimethylammonium, dicamba-isopropylammonium, dicamba-diglycolamine, dicamba-olamine, dicamba-diolamine, and dicamba-trolamine. Examples of a suitable ester are dicamba-methyl and dicamba-butoyl.

For a composition that includes glyphosate, application of the composition to a plant, plant part, area of cultivation, or any combination thereof is, according to one embodiment, carried out at a rate of between about 1 g/ha and about 2500 g/ha of glyphosate, or between about 5 g/ha and about 1500 g/ha glyphosate, or between about 100 g/ha and about 750 g/ha of glyphosate.

For a composition of the present invention that includes dicamba, application of the composition to a plant, plant part, area of cultivation, or any combination thereof is, according to one embodiment, carried out at a rate of between about 1 g/ha and about 1500 g/ha, or between about 5 g/ha and about 750 g/ha, or between about 50 g/ha and about 500 g/ha.

For a composition of the present invention that includes glufosinate, application of the composition to a plant, plant part, area of cultivation, or any combination thereof is, according to one embodiment, carried out at a rate of between about 1 g/ha and about 1000 g/ha, or between about 5 g/ha and about 500 g/ha, or between about 20 g/ha and about 300 g/ha, or between about 30 g/ha and about 200 g/ha.

Applying thiophanate methyl and an isolated HR elicitor protein or polypeptide fragment according to the method of the present invention can be carried out in the absence of pest (e.g., fungal pathogen) pressure and/or both before and after an infection of the materials or plants by any pest (e.g., fungal pathogen).

Applying thiophanate methyl and an isolated HR elicitor protein or polypeptide fragment according to the method of the present invention may occur at various different growth stages of the plant depending on the desired effect.

The term "growth stage" (GS) refers to the extended BBCH-scale, which is a system for a uniform coding of phenologically similar growth stages of all mono- and dicotyledonous plant species in which the entire developmental cycle of the plants is subdivided into clearly recognizable and distinguishable longer-lasting developmental phases. The BBCH-scale uses a decimal code system, which is divided into principal and secondary growth stages. The abbreviation BBCH derives from the Federal Biological Research Centre for Agriculture and Forestry (Germany), the Bundessortenamt (Germany) and the chemical industry.

Applying may be carried out at a growth stage (GS) between GS 00 and GS 73 BBCH, GS00 and GS 63 BBCH, GS11 and GS 63 BBCH, or GS 11 and GS 34 BBCH.

Applying may be carried out repeatedly, e.g., in 2, 3, 4, 5, 6, 7, 8, or more applications. In one embodiment, thiophanate methyl and an isolated HR elicitor protein or polypeptide fragment are applied first between BBCH growth stages 11 to 63 and again between BBCH growth stages 65 to 75.

Applying thiophanate methyl and an isolated HR elicitor protein or polypeptide fragment may be carried out by foliar spray treatment, in-furrow application, or by any other means.

According to the present invention, simultaneous (i.e., joint or separate) application of thiophanate methyl and an isolated hypersensitive response elicitor protein or polypeptide fragment (and, optionally, an additional active compound) and successive application of thiophanate methyl and an isolated hypersensitive response elicitor protein or polypeptide fragment (and, optionally, an additional active compound) enhance and/or increase the health of a plant compared to what is possible by applying either thiophanate methyl or an isolated hypersensitive response elicitor protein or polypeptide fragment alone. The active compounds thiophanate methyl and an isolated hypersensitive response elicitor protein or polypeptide fragment have a synergistic effect on plant yield, meaning that they are used in a quantity which gives the desired effect, which is a synergistic increase of the health of a plant but which preferably does not give rise to any phytotoxic symptom on the treated plant.

In carrying out the method of the present invention, the overall health of a plant is increased due the synergistic effect of applying thiophanate methyl and an isolated hypersensitive response elicitor protein or polypeptide fragment to a plant and/or area of cultivation. A synergistic effect is where the purely additive effect (in mathematical terms) of the application of the individual components is surpassed by the application of the combination (see FIGS. 1-2).

As used herein, "health of a plant" or "plant health" means the condition of a plant and/or its products which is determined by several aspects alone or in combination with each other, such as increased yield, plant vigor, quality, and tolerance to abiotic and/or biotic stress.

A plant suffering from fungal or insecticidal attack often produces a smaller biomass, which leads to a reduced yield as compared to a plant which has been subjected to curative or preventive treatment against the pathogenic fungus or any other relevant pest and which can grow without the damage caused by the biotic stress factor. However, applying thiophanate methyl and an isolated hypersensitive response elicitor protein or polypeptide fragment pursuant to the method of the present invention leads to enhanced plant health even in the absence of any biotic stress. This means that the positive effects of thiophanate methyl and an isolated hypersensitive response elicitor protein or polypeptide fragment cannot be explained just by the fungicidal, insecticidal, and/or herbicidal activities of the active ingredients, but is based on further activity profiles. As a result, application of thiophanate methyl and an isolated hypersensitive response elicitor protein or polypeptide fragment to a plant and/or area of cultivation can also be carried out in the absence of pest pressure on the plant.

According to the present invention, "increasing yield of a plant" means that the yield of a product of the plant is increased by a measurable amount over the yield of the same product of the plant produced under the same conditions, but without application of both thiophanate methyl and an isolated hypersensitive response elicitor protein or polypeptide fragment to the plant and/or area of cultivation. In one embodiment, the term "yield" refers to fruits in the proper sense, as well as vegetables, nuts, grains, and seeds.

"Grain" and "fruit" are to be understood as any plant product which is further utilized after harvesting, e.g., fruits in the proper sense, vegetables, nuts, grains, seeds, wood (e.g., in the case of silviculture plants), flowers (e.g., in the case of gardening plants and ornamentals), etc., meaning anything of economic value that is produced by the plant.

Increased yield of a plant can be characterized by the following non-limiting properties: increased plant weight; increased biomass, such as higher overall fresh weight (FW) and/or higher overall dry weight (DW); increased number of flowers per plant; higher grain and/or fruit yield; more tillers or side shoots (branches); larger leaves; increased shoot growth; increased protein content; increased oil content; increased starch content; increased pigment content; increased chlorophyll content; and any combination thereof.

Chlorophyll content has a positive correlation with a plant's photosynthesis rate and, accordingly, the higher the chlorophyll content the higher the yield of a plant.

According to one embodiment, a synergistic increase in yield in dry beans is greater than about 23%, 24%, 25%, 26%, 27%, 28%, 29%, 30%, or more compared to plants where no thiophanate methyl and isolated hypersensitive response elicitor protein or polypeptide fragment is applied to the plant and/or area of cultivation.

According to another embodiment, a synergistic increase in yield in peanut is greater than about 2%, 3%, 4%, or more compared to plants where no thiophanate methyl and isolated hypersensitive response elicitor protein or polypeptide fragment is applied to the plant and/or area of cultivation.

Increasing the yield of a plant may involve improving plant vigor. Plant vigor becomes manifest in several aspects, including the general visual appearance of the plant. Improved plant vigor can be characterized by, inter alia, the following: improved vitality of the plant; improved plant growth; improved plant development; improved visual appearance; improved plant stand (less plant verse/lodging); improved emergence; enhanced root growth and/or more developed root system; enhanced nodulation, in particular rhizobial nodulation; bigger leaf blade; bigger size; increased plant height; increased tiller number; increased number of side shoots; increased number of flowers per plant; increased shoot growth; increased root growth (extensive root system); enhanced photosynthetic activity; enhanced pigment content; earlier flowering; earlier fruiting; earlier and improved germination; earlier grain maturity; fewer non-productive tillers; fewer dead basal leaves; less input needed (such as fertilizers or water); greener leaves; complete maturation under shortened vegetation periods; less fertilizer needed; fewer sowing of seeds needed; easier harvesting; faster and more uniform ripening; longer shelf-life; longer panicles; delay of senescence; stronger and/or more productive tillers; better extractability of ingredients; improved quality of seeds (for being seeded in the following seasons for seed production); reduced production of ethylene and/or the inhibition of its reception by the plant; and any combination thereof.

Enhanced photosynthetic activity of a plant may be based on increased stomatal conductance and/or an increased $CO_2$ assimilation rate of the plant.

Increasing the yield of a plant may involve improving the quality of a plant and/or its products. Improvements in plant quality may include, without limitation, improving certain plant characteristics, such as increasing the content and/or composition of certain ingredients by a measurable or noticeable amount over the same factor of the plant produced under the same conditions, but without application of the composition of the present invention. Enhanced quality can be characterized by, inter alia, the following: increased nutrient content; increased protein content; increased content of fatty acids; increased metabolite content; increased carotenoid content; increased sugar content; increased amount of essential amino acids; improved nutrient composition; improved protein composition; improved composition of fatty acids; improved metabolite composition; improved carotenoid composition; improved sugar composition; improved amino acids composition; improved or optimal fruit color; improved leaf color; higher storage capacity; higher processability of the harvested products; or any combination thereof.

Increasing the yield of a plant may involve improving a plant's tolerance or resistance to biotic and/or abiotic stress factors. Biotic and abiotic stress, especially over longer terms, can have harmful effects on plants. Biotic stress is caused by living organisms while abiotic stress is caused, for example, by environmental extremes. In one embodiment, applying the composition of the present invention to a plant pursuant to the method of the present invention enhances tolerance or resistance to biotic and/or abiotic stress factors, meaning: (1) certain negative factors caused by biotic and/or abiotic stress are diminished in a measurable or noticeable amount as compared to plants exposed to the same conditions, but without being treated with an inventive mixture and (2) the negative factors are not diminished by a direct action of the composition on the stress factors, e.g., by its fungicidal or insecticidal action which directly destroys the microorganisms or pests, but rather by a stimulation of the plants' own defensive reactions against said stress factors.

Negative factors caused by biotic stress, such as pathogens and pests, are widely known and range from dotted leaves to total destruction of the plant. Biotic stress can be caused by living organisms, such as pests (e.g., insects, arachnides, and nematodes), competing plants (e.g., weeds), microorganisms (e.g., phytopathogenic fungi and/or bacteria), and/or viruses.

Negative factors caused by abiotic stress are also well-known and can often be observed either as reduced plant vigor (as described above) or by the following symptoms: dotted leaves, "burned" leaves, reduced growth, fewer flowers, less biomass, less crop yield, reduced nutritional value of the crop, and later crop maturity, to give just a few examples. Abiotic stress can be caused by, inter alia: extremes in temperature such as heat or cold (heat stress/cold stress), strong variations in temperature, temperatures unusual for the specific season, drought (drought stress), extreme wetness, high salinity (salt stress), radiation (e.g., by increased UV radiation due to the decreasing ozone layer), increased ozone levels (ozone stress), organic pollution (e.g., by phytotoxic amounts of pesticides), inorganic pollution (e.g., by heavy metal contaminants), and any combination thereof.

Biotic and/or abiotic stress factors decrease the quantity and the quality of the stressed plants, their crops, and fruits. As far as quality is concerned, reproductive development can be affected with consequences on the crops which are important for fruits or seeds. Synthesis, accumulation, and storage of proteins are mostly affected by temperature; growth is slowed by almost all types of stress; polysaccharide synthesis, both structural and storage, is reduced or modified. These effects result in a decrease in biomass (yield) and in changes in the nutritional value of the plant product.

The above identified indicators for the health condition of a plant may be interdependent and may result from each other. For example, an increased resistance to biotic and/or abiotic stress may lead to a better plant vigor, e.g., to better and bigger crops, and thus to an increased yield. Inversely, a more developed root system may result in an increased resistance to biotic and/or abiotic stress.

Applying thiophanate methyl and an isolated hypersensitive response elicitor protein or polypeptide fragment to a plant and/or area of cultivation has a synergistic effect on the plant to: increase the health of the plant, increase the yield of the plant, increase the biomass of the plant, increase the oil content of the plant, increase the vigor of the plant, increase the stand of the plant, increase the emergence of the plant, increase the root growth of the plant, increase the photosynthetic activity of the plant, improve the quality of the plant, improve the nutrient composition of the plant, improve the protein composition of the plant, improve the carotenoid composition of the plant, increase the tolerance of the plant to biotic stress, increase the tolerance of the plant to fungi, increase the tolerance of the plant to nematodes, increase the tolerance of the plant to bacteria, increase the tolerance of the plant to abiotic stress, increase the tolerance of the plant to drought stress, increase the tolerance of the plant to cold stress, increase the tolerance of the plant to heat stress, increase the tolerance of the plant to salt stress, increase the tolerance of the plant to ozone stress, and/or any combination thereof.

One of the most important factors for increased resistance against biotic and abiotic stress is the stimulation of the plant's natural defense reactions, which occurs by application of thiophanate methyl and an isolated hypersensitive response elicitor protein or polypeptide fragment according to the method of the present invention.

It is also possible for thiophanate methyl and an isolated hypersensitive response elicitor protein or polypeptide fragment (and, optionally, additional active compounds) to be packaged and used as a combination composition. Thus, another aspect of the present invention relates to a kit comprising formulated thiophanate methyl and an isolated hypersensitive response elicitor protein or polypeptide fragment (and, optionally, additional active compounds).

In one embodiment, the kit may include one or more, including all, components that may be used to prepare an agrochemical composition containing thiophanate methyl and an isolated hypersensitive response elicitor protein or polypeptide fragment (and, optionally, additional active compounds). For example, the kit may include thiophanate methyl and an isolated hypersensitive response elicitor protein or polypeptide fragment (and, optionally, an additional active compound) and/or an adjuvant component and/or a further pesticidal compound (e.g., insecticide, fungicide, or herbicide) and/or a growth regulator component. One or more of the components may already be combined together or pre-formulated.

In those embodiments where more than two active compounds are provided in a kit, the active compounds may already be combined together and as such are packaged in a single container such as a vial, bottle, can, pouch, bag, or canister. In an alternative embodiment, two or more active compounds may be packaged separately (i.e., not pre-formulated). As such, kits may include one or more separate containers such as vials, cans, bottles, pouches, bags, or canisters, each container containing a separate component for an agrochemical composition. In both forms, a component of the kit may be applied separately from or together with the further components or as a component of a combination composition.

The user may then apply the composition(s) usually from a predosage device, a knapsack sprayer, a spray tank, or a spray plane. Here, the agrochemical composition is made up with water and/or buffer to the desired application concentration, it being possible, if appropriate, to add further auxiliaries, and the ready-to-use spray liquid or the agrochemical composition according to the invention is thus obtained. In one embodiment, about 50 to about 500 liters of the ready-to-use spray liquid are applied per hectare of agricultural useful area, or about 50 to about 400 liters.

In another embodiment, either individual compounds formulated as a composition or partially premixed compounds (e.g., thiophanate methyl and an isolated hypersensitive response elicitor protein or polypeptide fragment (and, optionally, an additional active compound)) are mixed by the user in a spray tank and further auxiliaries and additives are added, if appropriate (tank mix).

In another embodiment, individual compounds (e.g., thiophanate methyl and an isolated hypersensitive response elicitor protein or polypeptide fragment (and, optionally, an additional active compound)) or partially premixed compounds (e.g. thiophanate methyl and an isolated hypersensitive response elicitor protein or polypeptide fragment (and, optionally, an additional active compound)) are applied jointly (e.g., after tank mix) or consecutively.

These aspects of the present invention are further illustrated by the examples below.

EXAMPLES

The following examples are provided to illustrate embodiments of the present invention, but they are by no means intended to limit its scope.

Example 1

Control of White Mold in Pinto Bean Plants with PHC-351 and Thiophanate Methyl The objective of this Example is to provide answers to the following questions: When applied at the specific timing, does PHC-351 affect the visual appearance of the crop? Does PHC-351 affect yield when applied at the specified timing? Does PHC-351 reduce white mold (*Sclerotinia sclerotiorum*) incidence or severity when applied at the specified timing? Is there an interaction between Topsin® M 70WP and PHC-351 in terms of white mold (*Sclerotinia sclerotiorum*) management and overall plant yield?

Materials

PHC-351 contains the harpin fusion protein of SEQ ID NO:1, which is a plant elicitor. In this trial, it was tested as a foliar spray on dry bean plants, in combination with Topsin® M treatment. Topsin® M 70WP is a thiophanate-methyl fungicide 70% Wettable Powder. Previous trials indicate that the timing specified in this protocol is later than desirable for influencing crop set. To influence plant growth and yield, harpin is normally applied at an earlier stage of plant development, the vegetative phase, which is prior to the development of fruiting bodies. Here it was applied at a later stage where the fruiting body was already in existence.

Plot Establishment and Test Layout

The test was initiated on a number of test sites suitable for dry bean production, and likely to have white mold. The sites had dry beans with white mold the previous year, and was not plowed the year of the test. Pinto varieties with a tolerance for white mold (such as 'Chase') were avoided.

Plot size, row spacing, and buffers: 6 rows (15-30" spacing=10 ft wide)×25+ ft plots. At least 5 ft down row between blocks. The 2 outer rows on both sides of the plot were buffers or borders that were not harvested.

Trial design: Plant 8 reps. Use a Randomized complete block design. After the 14 day stand count, block the plots based on stand.

Planting Date: Seed was planted within a commercially acceptable planting window.

Plant Density: This trial emphasizes yield; consequently, planting was to achieve highly uniform plant spacing down the row.

Site Management: Plant growth (fertilizer), insects, diseases, and weeds were managed according to locally accepted practices and within the other limitations mentioned in this protocol. All plots were managed identically, and test sites were managed to grow healthy plants while minimizing harmful impact of pests.

Mixing and Application

Spray Application: Treatments were applied with properly calibrated ground equipment equipped with a shielded spray boom to minimize spray drift. With 5 ft wide, 2-row spray boom having 3 nozzles spaced ~18-20 inches apart, the center two rows of each plot were sprayed. Boom width was adjusted to fit row spacing.

Rinsing: All mixing and application equipment was carefully triple rinsed prior to spraying plots and spray system was triple rinsed before switching to the next treatment. Spray treatments were carried out in the order of the Treatment List (Table 4).

Water Volume and Source: 20-30 gpa. Sprayed to ensure thorough coverage of the blooms, using drop nozzles if available. If tank water was high in total mineral content, salinity, and/or suspended solids, clean water was used.

Tank Mixtures: PHC-351 was applied to appropriate plots and treatments were allowed to dry. Then, Topsin® M 70WP was applied to appropriate plots. No other materials were added to these treatments.

PHC-351 Handling: Product was used within 8 hours of mixing. For replicated trial purposes: opened packets were used within 8 hrs. After opening, what was needed for the application was used, and the remaining material was discarded. Sprays were made on a day and at a time when the plants were actively growing.

Treatment Timing: Application was made to achieve thorough coverage of the blooms at the timing specified in treatment list, i.e., when 100% of the plants had at least 1 open bloom.

TABLE 4

Treatment List

| | Treatment | Rate | Rate Unit | Timing |
|---|---|---|---|---|
| 1 | Water Control* | | | Apply when 100% of the plants have 1 open bloom |
| 2 | PHC-351 | 1 | Oz/acre | Apply when 100% of the plants have 1 open bloom |
| 3 | Topsin ® M | 1.5 | lb/acre | Apply when 100% of the plants have 1 open bloom |
| 4 | PHC-351 | 1 | Oz/acre | Apply when 100% of the plants have 1 open bloom |
| 4 | Topsin ® M | 1.5 | lb/acre | |

*The water control should be treated with water at the same time as the chemical treatments.

Data Collection

At Planting—Composite Soil Sample: A composite soil sample was collected and analyzed 0-7 days before planting. The sample was intended to characterize the entire trial site. 20 soil cores were extracted randomly from across the planting area of the field trial and cores were mixed. The soil cores were submitted to an accredited lab and requested analysis for Organic Matter, micronutrients, macronutrients, soil pH, calculated Cation Exchange Capacity, and % Cation Saturation. The samples were handled as per standard soil analysis guidelines.

In-Season Counts: These measurements were requested to determine if there were early visual effects associated with the treatments.

(a) Plant stand counted at 14 and 28 Days After Emergence (DAE), counted entire length of two rows, then converted and reported as plants/acre. Used the 14 day count to block replicates, that is, had the same or nearly the same stand count for all entries within a replicate.

(b) Vigor (1-9) at 14 and 28 DAE by visually estimating vigor.

(c) Percent canopy closure at bloom, recorded for center two rows.

Disease Incidence and Severity: 10-14 days before harvest both the incidence of white mold in percent infected plants, and the severity were rated on a 1-5 scale, where 1 is the least severe and 5 is the most severe.

Yield: The center 2 rows of each plot were machine harvested. Harvest was within customary window and harvest delays were avoided. To minimize edge effects, harvesting was avoided the first and last 2.5 feet of each plot. Report was made of bean weight per plot and moisture content (%). After correcting for moisture, yield was calculated and reported as bushels per acre (bu/A).

Statistical Analysis: ANOVA and Fishers Protected LSD, P=0.10.

Experimental results are reported in FIG. 1.

The trials were completed in dry bean production regions where white mold is frequently a problem. 2012 was hotter and drier than normal at 6 of the sites, and colder and wetter than normal at the remaining sites. Pre-spray data showed no difference in stand, vigor, or canopy closure, indicating no unusual pre-existing plot variability. White mold appeared at 5 of the sites (in WA, WI, MI, & ID). Overall when PHC-351 (Harpin) was applied alone it increased the yield by an average of 3.59% over the untreated control. When Topsin® M (Thiophanate Methyl) was applied alone it increased the yield by 18.6% over the untreated control. However, when they were both used on the plant, the yield increased by more than the sum of 3.59% and 18.6%. The yield increase for the combination was 25.1%; this is nearly 3% more than what would be predicted, demonstrating an unexpected and synergistic result. Similar results would be expected for any other dry bean variety.

Example 2

Influence on Yield and Leaf Spot Control in Runner-Type Peanut Plants with PHC-351 and Thiophanate Methyl The objective of this Example is to provide answers to the following questions: When applied at the specific timing, does PHC-351 affect the visual appearance of the crop? Does PHC-351 affect yield when applied at the specified timing? Does PHC-351 reduce white mold (Early=*Cercospora*, Late=*Cerosporidium*) incidence or severity when applied at the specified timing? Is there an interaction between Topsin® M and PHC-351 in terms of white mold (Early=*Cercospora*, Late=*Cerosporidium*) management and overall plant yield?

Materials

PHC-351 contains the harpin fusion protein of SEQ ID NO:1, which is a plant elicitor. In this trial, it was tested as a foliar spray on Runner-Type peanut plants, in combination with Topsin® M treatment. Topsin® M 70WP is a thiophanate-methyl fungicide 70% Wettable Powder. Previous trials indicate that the timing specified in this protocol is later than desirable for influencing crop set. To influence plant growth and yield, harpin is normally applied at an earlier stage of plant development, the vegetative phase, which is prior to the development of fruiting bodies. Here it was applied at a later stage where the fruiting body was already in existence.

Plot Establishment and Test Layout

The test was initiated on a test site suitable for Runner Type peanut production, and likely to have leaf spot.

Plot size, row spacing, and buffers: 6 rows (36" spacing=18 ft wide)×30+ ft plots. At least 10 ft alley was left between blocks. The 2 outer rows on both sides of the plot were borders that were not treated or harvested.

Trial design: Planted 6 reps. Used a Randomized complete block design. The plots were blocked based on uniform stand.

Planting Date: Seed was planted within a commercially acceptable planting window.

Plant Density: This trial emphasizes yield; consequently, planting was to achieve highly uniform plant spacing down the row.

Site Management: Insects, diseases, and weeds were managed according to locally accepted practices and within the other limitations mentioned in this protocol. All plots were managed identically, and test site was managed to grow healthy plants while minimizing harmful impact of pests. The entire trial area was sprayed with other fungicides (chlorothalonil) to control diseases.

Mixing and Application

Spray Application: Treatments were applied with properly calibrated ground equipment equipped with a shielded spray boom to minimize spray drift. With 6 ft wide, 2-row spray boom having 6 nozzles spaced ~18-24 inches apart, the center four rows of each plot were sprayed. Boom width was adjusted to fit row spacing.

Rinsing: All mixing and application equipment was carefully triple rinsed prior to spraying plots and spray system was triple rinsed before switching to the next treatment. Spray treatments were carried out in the order of the Treatment List (Table 5).

TABLE 5

Treatment List

| Treatment | Rate | Rate Unit | Timing |
|---|---|---|---|
| 1 Water Control* | | | Apply at 35-40 DAE and repeat on 14 day intervals as needed for leaf spot control. Apply at least 3 applications. |
| 2 PHC-351 | 1 | Oz/acre | Apply at 35-40 DAE and repeat on 14 day intervals as needed for leaf spot control. Apply at least 3 applications. |
| 3 Topsin ® M | 0.5 | lb/acre | Apply at 35-40 DAE and repeat on 14 day intervals as needed for leaf spot control. Apply at least 3 applications. |
| 4 PHC-351 | 1 | Oz/acre | Apply at 35-40 DAE and repeat on 14 day intervals as needed for leaf spot control. Apply at least 3 applications. |
| 4 Topsin ® M | 0.5 | lb/acre | Apply at 35-40 DAE and repeat on 14 day intervals as needed for leaf spot control. Apply at least 3 applications. |

*The water control should be treated with water at the same time as the chemical treatments.

Water Volume and Source: 15-20 gpa. Sprayed to ensure thorough coverage of the foliage. If tank water was high in total mineral content, salinity, and/or suspended solids, clean water was used.

Tank Mixtures: PHC-351 was applied to appropriate plots and treatments were allowed to dry. Then, Topsin® M was applied to appropriate plots. No other materials were added to these treatments.

PHC-351 Handling: Product was used within 8 hours of mixing. For replicated trial purposes: opened packets were used within 8 hrs. After opening, what was needed for the application was used, and the remaining material was discarded. Sprays were made on a day and at a time when the plants were actively growing.

Treatment Timing: Application was made 35-40 DAE and repeated on 14 day intervals as needed for leaf spot control. At least 3 applications were made. No more than 2 lbs./A of Topsin® were applied per season.

Data Collection

At Planting—Composite Soil Sample: A composite soil sample was collected and analyzed 0-7 days before planting. The sample was intended to characterize the entire trial site. 20 soil cores were extracted randomly from across the planting area of the field trial and cores were mixed. The soil cores were submitted to an accredited lab and requested analysis for Organic Matter, micronutrients, macronutrients, soil pH, calculated Cation Exchange Capacity, and % Cation Saturation. The samples were handled as per standard soil analysis guidelines.

In-Season Counts: These measurements were requested to determine if there were early visual effects associated with the treatments.

(a) Plant stand counted at 28 Days After Emergence (DAE), counted entire length of two rows, then converted and reported as plants/acre. Used the 28 day count to block replicates, that is, had the same or nearly the same stand count for all entries within a replicate.

(b) Vigor (1-9) at 28 DAE by visually estimating vigor for entire plot (1=poorest and 9=best).

Disease Incidence and Severity: Leaf spot was rated at 30 days before harvest and again at 5-7 days before harvest. Both the incidence of Leaf Spot (Early=*Cercospora*, Late=*Cerosporidium*) in percent infected plants, and the severity on a 1-10 scale was reported, where 1 is the least severe and 10 is the most severe.

Yield: The center 2 rows of each plot were machine harvested. Harvest was within customary window and harvest delays were avoided. Report was made of peanut weight per plot and yield was calculated and reported as pounds per acre (lbs/A).

Statistical Analysis: ANOVA and Fishers Protected LSD, P=0.10.

Experimental results are reported in FIG. 2.

The trials were conducted according to the protocol as described above. The disease pressure (Late Leaf Spot *Mycosphaerella berkeleyi*) was low to moderate in these trials. Yields were recorded and were noted to be very high and similar in the two locations. The PHC-351 treatment was shown to reduce yield slightly (by 5.3% or 311 lbs). However, the Topsin® M (Thiophanate Methyl) treatment increased yield slightly; when applied alone Topsin® M increased yield by 3.0% over the untreated control (177 lbs). It was surprising to see that despite the fact that PHC-351 caused a mild deleterious effect to yield when applied alone, when it was applied in combination with Thiophanate Methyl the yield increased by 3.7% over the untreated control (218 lb). The combination increased yield more than either of the products did separately, or additively, displaying clear synergy.

Although the invention has been described in detail for the purpose of illustration, it is understood that such detail is solely for that purpose, and variations can be made therein by those skilled in the art without departing from the spirit and scope of the invention which is defined by the following claims.

What is claimed:

1. A composition comprising a liquid or solid carrier, thiophanate methyl, and an isolated hypersensitive response elicitor harpin protein or polypeptide fragment.

2. The composition according to claim 1, wherein the carrier is a liquid carrier.

3. The composition according to claim 1, wherein the carrier is a solid carrier.

4. The composition according to claim 1, wherein the composition is in the form of a solution, emulsion, suspension, dust, powder, paste, or granule.

5. The composition according to claim 1 further comprising:
an effective amount of an additional insecticide, an additional fungicide, an herbicide, a plant growth regulator, or a combination thereof.

6. The composition according to claim 5, wherein the composition comprises an effective amount of an herbicide selected from glyphosate, dicamba, glufosinate, agriculturally acceptable salts and esters thereof, or a combination thereof.

7. The composition according to claim 1, wherein the hypersensitive response elicitor harpin protein or polypeptide fragment is recombinant.

8. The composition according to claim 1, wherein the hypersensitive response elicitor harpin protein or polypeptide fragment comprises a full-length hypersensitive response elicitor harpin protein.

9. The composition according to claim 1, wherein the hypersensitive response elicitor harpin protein or polypeptide fragment comprises a fusion protein.

10. The composition according to claim 9, wherein said fusion protein comprises an isolated pair or more of spaced apart domains, each comprising an acidic portion linked to an alpha-helix.

11. The composition according to claim 10, wherein each domain is from a different source organism.

12. The composition according to claim 10, wherein there are 3 or more spaced apart domains.

13. The composition according to claim 10, wherein at least one domain is selected from the group of domain sequences consisting of A, $N_N$, $N_C$, W, $Z_N$, and $Z_{266-308}$.

14. The composition according to claim 13, wherein the fusion protein comprises an ordered group of domain sequences selected from the group consisting of $W(N_N)_4A(N_C)_4Z_{266-308}$, $W(N_N)_4Z_N(N_C)_4Z_{266-308}$, and $W(N_N)_4Z_N(N_C)_4Z_{266-308}A$.

15. The composition according to claim 9, wherein the fusion protein has an amino acid sequence of SEQ ID NO:1.

16. The composition according to claim 1, wherein the hypersensitive response elicitor harpin protein or polypeptide fragment comprises structural characteristics selected from the group consisting of glycine rich, low or no cysteine content, heat stable, hydrophilic, lacking an N-terminal signal sequence, susceptible to proteolysis, and combinations thereof.

17. The composition according to claim 1, wherein the composition is capable of inducing a synergistic yield in a plant to which the composition is applied.

\* \* \* \* \*